(12) United States Patent
Bauer et al.

(10) Patent No.: US 7,966,269 B2
(45) Date of Patent: Jun. 21, 2011

(54) INTELLIGENT HUMAN-MACHINE INTERFACE

(76) Inventors: James D. Bauer, Lebanon, OR (US);
Kenneth H. Funk, II, Corvallis, OR (US); Roberto Nicolalde Flores, West Labanon, NH (US)

( * ) Notice: Subject to any disclaimer, the term of this patent is extended or adjusted under 35 U.S.C. 154(b) by 350 days.

(21) Appl. No.: 11/255,593

(22) Filed: Oct. 20, 2005

(65) Prior Publication Data
US 2007/0136218 A1    Jun. 14, 2007

(51) Int. Cl.
*G06F 15/18* (2006.01)
(52) U.S. Cl. ............................................. 706/12; 706/46
(58) Field of Classification Search .......................... None
See application file for complete search history.

(56) References Cited

U.S. PATENT DOCUMENTS

| 2003/0028498 | A1* | 2/2003 | Hayes-Roth | 706/17 |
| 2006/0184473 | A1* | 8/2006 | Eder | 706/20 |
| 2006/0282302 | A1* | 12/2006 | Hussain | 705/9 |

FOREIGN PATENT DOCUMENTS
WO    PCT/US06/60138    10/2006

OTHER PUBLICATIONS

J. Fernandez-Lozano et al., Human-Machine Interface Evaluation in a Computer Assisted Surgical System, 2004, IEEE, 231-236.*
Karen Fitzgerald, Medical Electronics, 1991, IEEE, 76-78.*
Moji Ghodoussi et al., Robotic-Surgery-The Translantic Case, 2002,IEEE, 1882-1888.*
Kevin Cleary, Medical Robotics and the Operating Room of the Future, 2005, IEEE, 7250-7253.*
Sheetal Agarwal et al., A Pervasive Computing System for the Operating Room of the Future, No Date, UM Medical School, 1-16.*
"Flexible Frameworks for Medical Multimedia", Michael W. Halle, Ron Kikinis, International Multimedia Conference, Proc of the 12$^{th}$ annual ACM International Conference on Multimedia, MM' 04, Oct. 10-16, 2004, pp. 768-775.*
PCT/US06/60138 Notification of Transmittal of the International Search Report and Written Opinion of the International Searching Authority, dated Sep. 16, 2008 (1 pg). PCT/US06/60138 takes priority to U.S. Appl. No. 11/255,593.
PCT/US06/60138 International Search Report , dated Sep. 16, 2008 (4 pgs). PCT/US06/60138 takes priority to U.S. Appl. No. 11/255,593.

(Continued)

*Primary Examiner* — Donald Sparks
*Assistant Examiner* — Mai T. Tran
(74) *Attorney, Agent, or Firm* — Silicon Forest Patent Group; Paul J. Fordenbacher, Esq.

(57) ABSTRACT

Methods and apparatus for an intelligent human-machine interface comprising an interface shell, system agents, function agents, a dynamic documentation system, and a layering architecture. The system agents include dynamic, knowledge-based software object sub-agents that model and track the state of a work area. The function agents model, track, and facilitate work area functions. The interface shell provides a hardware and software interface between the system agents and the function agents. The layering architecture comprises a tracking layer, an equipment and supply management layer, a coordination layer, and a situational awareness layer, and an oversight layer. The oversight layer combines information from the situational awareness layer with process rule sets contained in the function agents to determine if processes are being performed correctly. The interface processes an integrated collection of facts and relationships and recognizes deviation from or compliance with a predetermined process and communicates the same to a user.

6 Claims, 22 Drawing Sheets

OTHER PUBLICATIONS

PCT/US06/60138 Written Opinion of the International Searching Authority, dated Sep. 16, 2008 (5 pgs). PCT/US06/60138 takes priority to U.S. Appl. No. 11/255,593.

PCT/US06/60138 International Preliminary Report on Patentability, dated Oct. 28, 2008 (6 pgs). PCT/US06/60138 takes priority to U.S. Appl. No. 11/255,593.

PCT/US06/60138 Invitation to Pay Additional Fees (to show groupings of inventions under Unity of Invention rules), dated Jun. 20, 2008 (2 pgs). PCT/US06/60138 takes priority to U.S. Appl. No. 11/255,593.

* cited by examiner

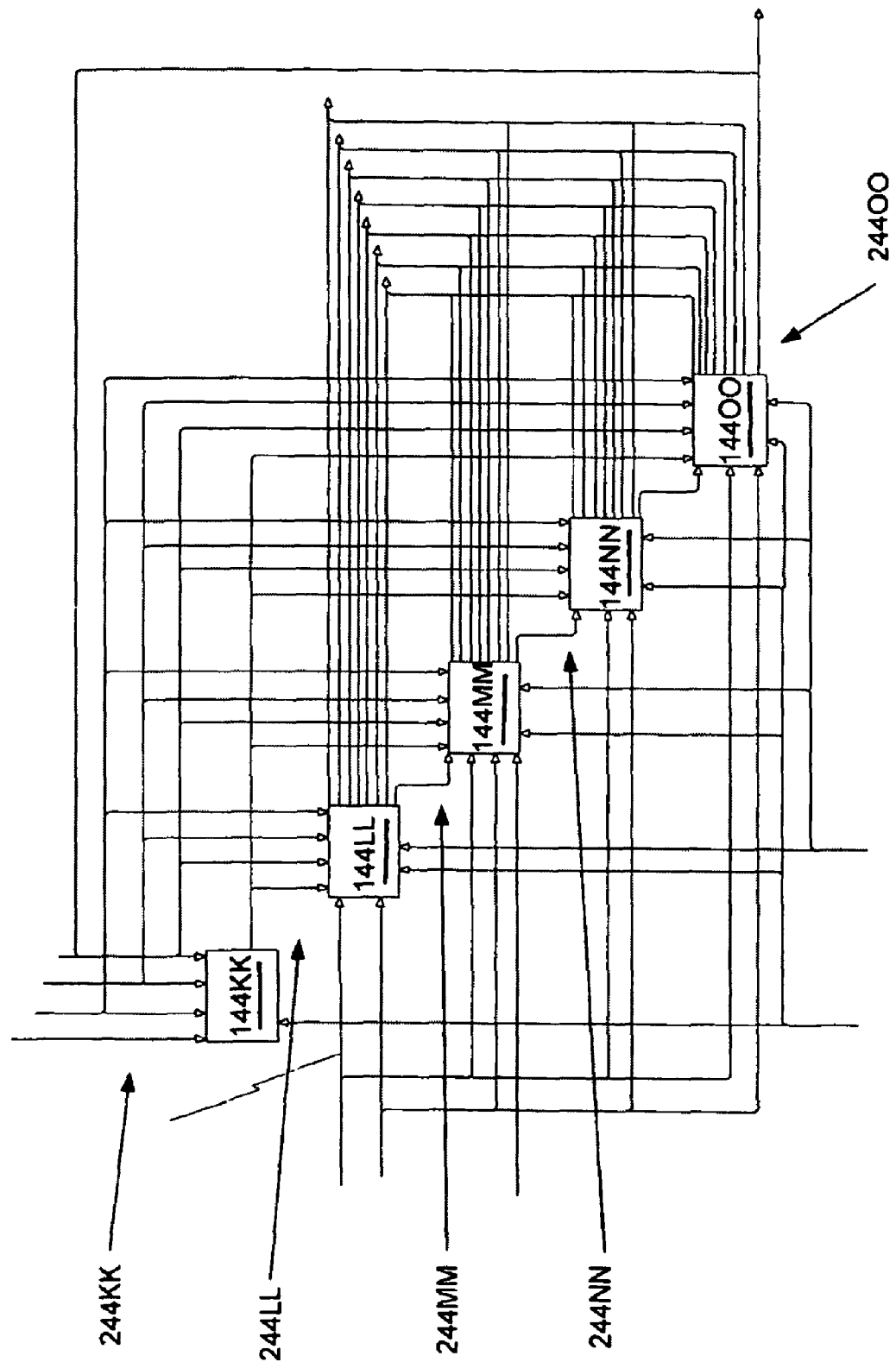

INTELLIGENT HUMAN-MACHINE INTERFACE

FIELD

The present invention is related to information and control systems, and more particularly, to systems and processes for real-time management and feedback of process control, situational awareness, logistics, communication, and documentation.

BACKGROUND

Technology and innovations have come to the healthcare industry in a haphazard fashion. The unplanned development of medical technology has cluttered both the physical operating room (OR) landscape and the surgeon's and other healthcare team member's mental mindscape with a disjoint collection of equipment and instruments. Subsequently, the unplanned development has created many gaps in the surgery's potential capabilities as well as fragmentation of the environment which harbors inefficiency, invites human-error, and suffers preventable mishaps. The OR clutter has resulted as a consequence of fragmentary innovations without commitment to any unifying design philosophy or overarching physical and sensory infrastructure. Essentially, the principles of human modeling and simulation (HMS) and human factors engineering have been ignored, thereby allowing piecemeal innovation to box the surgeon and process into a corner. The development of future healthcare environment must integrate HMS engineering principles into and throughout the design process so that we can produce a generation of truly "smart" instruments that serve critical process needs and procedures as opposed to offering another batch of simply "clever" gadgets.

All industries seek to define and implement quality processes as many activities move from a cottage industry to mature scientific endeavor. Management tools such as Total Quality Management (TQM), Six Sigma, and ISO 9000, among others, are difficult to uniformly apply until the processes of an industry have evolved to the point of specific definition, standardization, measurement, and optimization. For an industry to effectively and rapidly ramp up to the quality standards demanded by the world market place, requires a smart environment that complements the human decision making and compensates for both human fallibilities and systems vulnerabilities. Health care is a traditional industry that struggles to meet the quality demands of the twenty first century: effectiveness, efficiency (economy) and safety.

As healthcare leadership examines the delivery of healthcare in America, a glaring deficit emerges: the lack of modern safety systems to reduce the iatrogenic injuries inflicted in the delivery of care. The physicians, nurses, and support staff are not careless, but rather the entire system is vulnerable. The Institutes of Medicine released a report in 2000, estimating that 3.7 percent of all hospitalizations are marred by an adverse event and forty-three percent of those adverse events occurred in surgery, a disproportionately high rate compared to all hospitalized patients.

Analysis of the events indicates that 70 percent of these events were preventable. A significant number of patient deaths are attributed to medical error, 44,000 to 98,000 per year. Regardless of which set of numbers is judged to be more accurate, expert opinion is that the rate of medical error, particularly surgical error, must be controlled.

An explosion of new technical surgical equipment and associated intricate surgical procedures has created a complex, high-risk environment for the modern surgeon. It harbors inefficiency as well as systemic vulnerability to error. Human errors lead to patient morbidity, mortality, and other adverse events. Many of the activities within the OR are disjointed. There is a need to organize the personnel around the central task in order to focus their intellectual and physical efforts. The operating room is plagued by poor acoustics and a surgical site that cannot be readily visualized by many members of the OR team. Therefore, the constructive oversight and suggestions of all team members cannot be accomplished because most of the team is simply "left out" of the procedure.

The disconnect between the anesthesiologist, circulating nurse and the hospital support network causes innumerable inefficiencies, distractions, and interpersonal tensions. Logistical demands of complex surgery, particularly endoscopic surgery, aggravate this situation within the OR, leading to miscommunications, non-communication, lack of efficient teamwork, and general failure of the OR personnel to form an effective team.

The OR has evolved into a complex human-machine system in which traditional means of communication and control are no longer satisfactory. Now the human actors, including surgeons, anesthesiologists, and nursing staff, require an overarching system to facilitate their interactions, minimize errors, and allow the surgeon to concentrate on the task at hand: actually performing the surgical procedure. Confusion and lack of situational awareness on the part of all the OR team members degrades both safety and efficiency.

With complex equipment, people, and purposes, it is easy to see where conflict and difficulty maintaining healthy team dynamics arise. Humans have limits; there is a point at which multitasking becomes over-tasking. Furthermore, the rigid hierarchy has proven in many circumstances to inhibit subordinates from giving clues and corrections to obvious mistakes of the surgeon or anesthesiologist who are generally placed at the top of the hierarchical system. There are time pressures, safety concerns and basic tensions as the various player roles and parallel activities come together. Research shows that surgeons as well as other team members would prefer a more collaborative environment with team input and direction.

By way of example, looking at the transfer of materials, the circulator and scrub nurse provide the flow of instruments, implants and expendable items for the operation. They also clear specimens, unneeded instruments, and used expendables to reduce clutter. The circulator also completes a great deal of documentation including: basic paperwork recording surgical events and exact procedures performed, who is in the room, surgery start time, specimens, drugs administered, and material requisition and billing sheets.

The circulator shuttles between instrument and material storage rooms within and outside of the OR to obtain needed materials for the procedure. Outside shuttling is also facilitated by the OR clerk and manager who communicate with the hospital logistics system, the laboratory, radiology, among others, to provide material support.

The OR team does not function in a vacuum. During the course of surgery there are many messages relayed to the surgeon, anesthesiologist, and other team members. Some of these messages are pertinent to the surgery. Many are pertinent to other medical business or even personal business.

Neither the problems nor solutions are superficial. The problems are deeply buried in the details of the surgical process and the activities within the OR. They require a solution with intense observation, thoughtful analysis, re-engineering of the OR, and appropriate training of the actors.

What is needed in the art is an OR with: more effective, efficient, and safer processes, including planning, surgical, and anesthesia processes that do the right things correctly, quickly, and using scarce resources sparingly, so as to cause no undue harm to the patient; more complete, accurate, and timely situation awareness, including shared team knowledge of the patient, equipment, materials and supplies, processes, and team activities; more effective logistics, including a more proactive support process that provides what is needed, where it is needed, when it is needed; better communication about the state of the OR system and processes, team goals, requests, and directives; and more complete, accurate, and timely documentation that not only meets accounting and archiving purposes, but produces records in real-time that are immediately useful to the OR team through a process that is less time consuming and disruptive to other OR activities.

SUMMARY

An intelligent human-machine interface comprising an interface shell, a system agent and a function agent is provided in accordance with an embodiment of the present invention. The system agent includes one or more dynamic, knowledge-based software object sub-agents adapted to model and track the state of a work area. The function agent is adapted to model, track, and facilitate work area functions. The interface shell is adapted to provide a hardware and software interface between the system agent and the function agent. The intelligent human-machine interface is adapted to track the movement of specific instruments and actors. The intelligent human-machine interface is adapted to indicate key milestones in a work process.

In accordance with another embodiment, the intelligent human-machine interface further comprises means wherein voice recognition and specific workstation input identifies a human actor and holds the actor responsible for the accuracy and effort to accomplish a checklist-prescribed event. The interface shell is adapted to provide intelligent prompts projected on a monitor providing situational and logistics information.

In accordance with another embodiment, the intelligent human-machine interface further comprises a dynamic documentation system in communication with the function agents and system agents. The dynamic documentation system tracks events and anticipates the next likely step, cueing operator and team members.

In accordance with another embodiment, the intelligent human-machine interface further comprises a layering architecture, comprising a tracking layer, and equipment and supply management layer, a coordination layer, a situation awareness layer, and an oversight layer. The equipment and supply management layer adapted to take the information from the tracking layer and processes the information in regards to records, inventory and maintenance systems. The coordination layer is adapted to take information from the tracking layer and the equipment and supply management layer to develop an image of what is occurring in comparison to what an overall plan is based. The situational awareness layer is in communication with the tracking layer and adapted to provide output features to the various interfaces. The oversight layer is adapted to combine the information from the situational awareness layer with the function agents to determine if processes are being preformed correctly.

A method for providing an intelligent human-machine interface in accordance with an embodiment of the present invention comprises providing an interface shell, providing a system agent including one or more dynamic, knowledge-based software object sub-agents adapted to model and track the state of a work area, and providing a function agent adapted to model, track, and facilitate work area functions. The interface shell is adapted to provide a hardware and software interface between the system agent and the function agent. The method further comprises creating a system hierarchy model of the structural elements of a system and a functional model of the operating room, identifying a set of sensor, actuator, and communication systems necessary to implement functionality, identifying component and interface specifications for the acquisition and integration of the physical components, creating functional model software specifications, and utilizing a model based knowledge base to construct the hierarchy and operations.

In accordance with another embodiment, the method for providing an intelligent human-machine interface further comprises providing voice recognition and specific workstation input so as to identify a human actor and holds the actor responsible for the accuracy and effort to accomplish a checklist-prescribed event, the interface shell adapted to provide intelligent prompts projected on a monitor providing situational and logistics information.

In accordance with another embodiment, the method for providing an intelligent human-machine interface further comprises providing a layering architecture, comprising a tracking layer, an equipment and supply management layer adapted to takes the information from the tracking layer and processes the information in regards to records, inventory and maintenance systems, a coordination layer adapted to take information from the tracking layer and the equipment and supply management layer to develop an image of what is occurring in comparison to what an overall plan is based, a situational awareness layer in communication with the tracking layer and adapted to provide output features of the various interfaces, and an oversight layer adapted to combine the information from the situational awareness with the function agents to determine if processes are being preformed correctly.

An intelligent human-machine interface for a medical operating room comprising an interface shell, a system agent, and a function agent is provided in accordance with an embodiment of the present invention. The system agent includes one or more dynamic, knowledge-based software object sub-agents adapted to model and track the state of the operating room. The function agent is adapted to model, track, and facilitate operating room functions. The interface shell is adapted to provide a hardware and software interface between the system agent and the function agent. The intelligent human-machine interface is adapted to track the movement of specific instruments and actors. The intelligent human-machine interface is adapted to indicate key milestones in a work process.

In accordance with another embodiment, the intelligent human-machine interface further comprises means wherein voice recognition and specific workstation input identifies a human actor and holds the actor responsible for the accuracy and effort to accomplish a checklist-prescribed event. The interface shell is adapted to provide intelligent prompts projected on a monitor providing situational and logistics information.

In accordance with another embodiment, the intelligent human-machine interface further comprises a dynamic documentation system in communication with the function agents and system agents. The dynamic documentation system tracks surgical events and anticipates the next likely step, cueing operator and team members.

In accordance with another embodiment, the intelligent human-machine interface further comprises a layering architecture, comprising a tracking layer, and equipment and supply management layer, a coordination layer, a situation awareness layer, and an oversight layer. The equipment and supply management layer adapted to take the information from the tracking layer and processes the information in regards to records, inventory and maintenance systems. The coordination layer is adapted to take information from the tracking layer and the equipment and supply management layer to develop an image of what is occurring in comparison to what an overall plan is based. The situational awareness layer is in communication with the tracking layer and adapted to provide output features to the various interfaces. The oversight layer is adapted to combine the information from the situational awareness layer with the function agents to determine if processes are being preformed correctly.

In accordance with another embodiment, the intelligent human-machine interface further comprises a layer adapted to connect to other intelligent human-machine interfaces through the internet to create a library of correct and incorrect procedures with aims to facilitate machine learning.

In accordance with another embodiment, the intelligent human-machine interface further comprises means to transmit changes aimed at process optimization to all human actors, mechanical elements, and support systems in order to enhance quality.

In accordance with another embodiment, the intelligent human-machine interface further comprises means wherein the agent and object based software architecture provides easy adaptability and expandability for the fast and efficient transmission of information between agents in the form of software robots.

An RFID sensor sheet is provided in accordance with an embodiment of the present invention. The RFID comprises an antenna array coupled to a film, and electronics adapted to provide power and a communication means for coupling to RFID detection electronics and communication electronics to communicate sensor data to an access point connected to a computer platform that supports the system's RFID middleware. The antenna array is adapted to create a specific volume of space that an RFID tagged object will be reliably detected. The RFID sensor sheet is adapted to register the identity of an RFID tagged item place therein.

The RFID sensor sheet further comprises a wireless transceiver in accordance with another embodiment of the present invention. The RFID sensor sheet further comprises electronics comprising control means to adjust the gain of the antenna array to adjust the sensing volume above the surface in accordance with another embodiment of the present invention.

A tracking system is provided, comprising an RFID sensor sheet and a video tracking system, in accordance with an embodiment of the present invention. The RFID sensor sheet comprises an antenna array coupled to a film, and electronics adapted to provide power and a communication means for coupling to RFID detection electronics and communication electronics to communicate sensor data to an access point connected to a computer platform that supports the system's RFID middleware. The antenna array is adapted to create a specific volume of space that an RFID tagged object will be reliably detected. The video tracking system comprises a camera adapted to be located such that its field of view is able to image a work object that is placed on a work surface.

BRIEF DESCRIPTION OF THE DRAWINGS

Like reference numbers generally indicate corresponding elements in the figures.

FIGS. 6A-6I are schematic diagrams of underlying sub-function agents, in accordance with an embodiment of the present invention;

DETAILED DESCRIPTION

Figure 2:
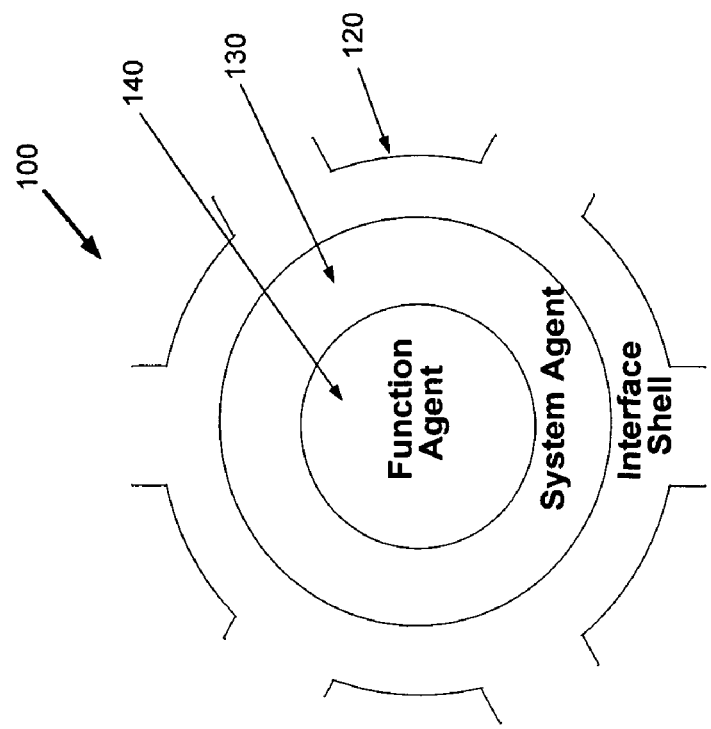
FIG. 2 is a schematic diagram showing the smart system as a layered structure comprising an interface shell, a system agent, and a function agent, in accordance with an embodiment of the present invention.

References will now be made to embodiments illustrated in the drawings and specific language which will be used to describe the same. It will nevertheless be understood that no limitation of the scope of the invention is thereby intended, such alterations and further modifications in the illustrated methods and apparatus, as such further applications of the principles of the invention as illustrated therein as being contemplated as would normally occur to one skilled in the art to which the invention relates.

Agent as used herein refers to a computer program that has the ability to perceive, reason and act in an autonomous manner in both a reactive and proactive fashion. A common view of an agent is that of an active object defined by a specific bounded process, and with the ability to communicate with other agents.

Autonomy as used herein refers to "under self-control".

Knowledge-Base as used herein refers to the language to communicate assertion about the real world and provides the structure to logically store data and process that resemble the real world elements, interactions and their interrelationships. Each agent's attributes and methods represent a subset of the Knowledge-Base and the interactions and relationships between agents complete the overall Knowledge-Base.

Agent architecture as used herein refers to a particular method to build agents, so they can perceive, reason, and act autonomously among a community of other agents.

Architecture as used herein refers to the particular arrangement of data, algorithms, and control flows, which the agent uses to decide what to do.

Layered agent architecture as used herein refers to the particular structure in which each agent's functions are arranged to accomplish multiple types of behavior, such as reactive behavior, pro-active behavior, logic based, behavior, cooperative behavior, among others.

System architecture as used herein refers to the structure or organization of the components (modules), the manner in which these components interact, and the structure of the data that is used by the components.

Interface shell as used herein refers to hardware and software required to host the agents and to link those agents with the structural (physical elements) of the environment.

Middleware as used herein refers to a collection of infrastructure components that enable communication of different system components.

System agents as used herein refers to agents that model and represent the physical components within the real world system of interest so as to keep track of the state of its physical and hence system components, to make that state information available to other agents, and to recognize and inform other agents about existing or predicted non-normal conditions of that system.

Function agent as used herein refers to a repository of intelligence that tracks and compares the real world process to its knowledge base with what the process should be for efficient, effective and safe execution.

Priority processing as used herein refers to the way in which agents determine the priority of execution within the community of other agents, with respect to precedence of error reporting, cuing and warning, among others.

Embodiments in accordance with the present invention relate to methods and apparatus for an intelligent human-machine interface. By way of example, but not limited thereto, embodiments of methods and apparatus are presented of an intelligent human-machine interface for the operating room (OR), and more particularly, to systems and processes for real-time management and feedback of process control, situational awareness, logistics, communication, and documentation, herein referred to as smart system 100. One element of the smart system 100, among others, provides a knowledge base that organizes information and rules that enables an accurate, relevant and timely decision support system. The knowledge base is represented in a hierarchical structure of functions and systems. The smart system 100 serves as platform for the avoidance, detection and timely correction of errors; and as such, acts as a countermeasure to error.

Figure 1:
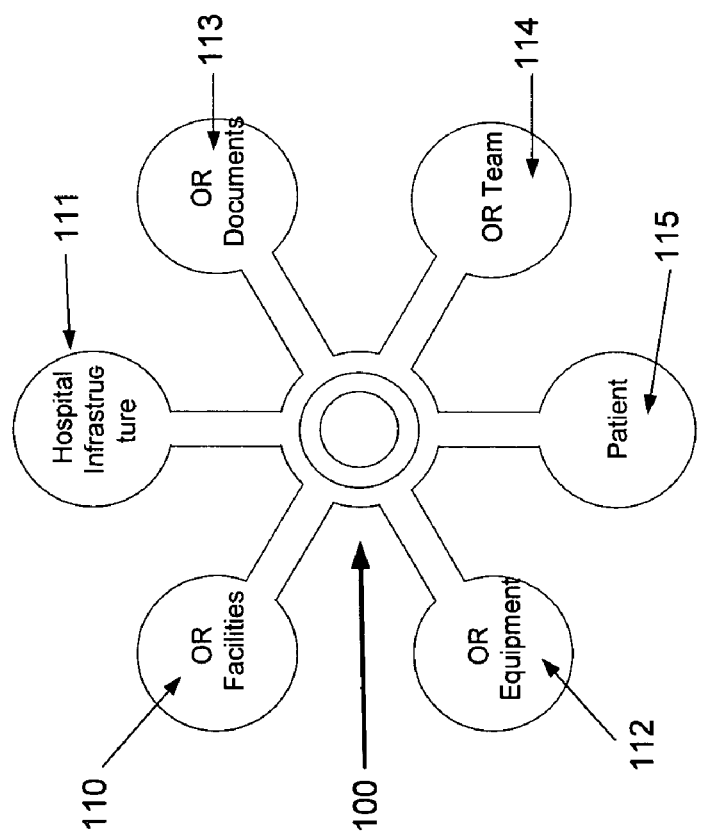
FIG. 1 is a schematic diagram showing the smart system as an interface for a plurality of OR elements, in accordance with an embodiment of the present invention.

FIG. 1 is a schematic diagram showing how smart system 100 presents as an interface for a plurality of OR elements, including, but not limited to, the OR facilities 110, hospital infrastructure 111, OR equipment 112, OR documents 113, OR team 114, and the patient 115, in accordance with an embodiment of the present invention.

FIG. 2 is a schematic diagram showing smart system 100 as a layered structure comprising an interface shell 120, a system agent 130, and a function agent 140, in accordance with an embodiment of the present invention. The interface shell 120 is a hardware and software interface between the systems, subsystems, and elements of the OR and the system agent 130 and the function agent 140. The interface shell 120 further comprises hardware and software required to host the system agent 130 and the function agent 140 and to link the function and system agents 130,140 with the structural elements of the OR.

Figure 3:
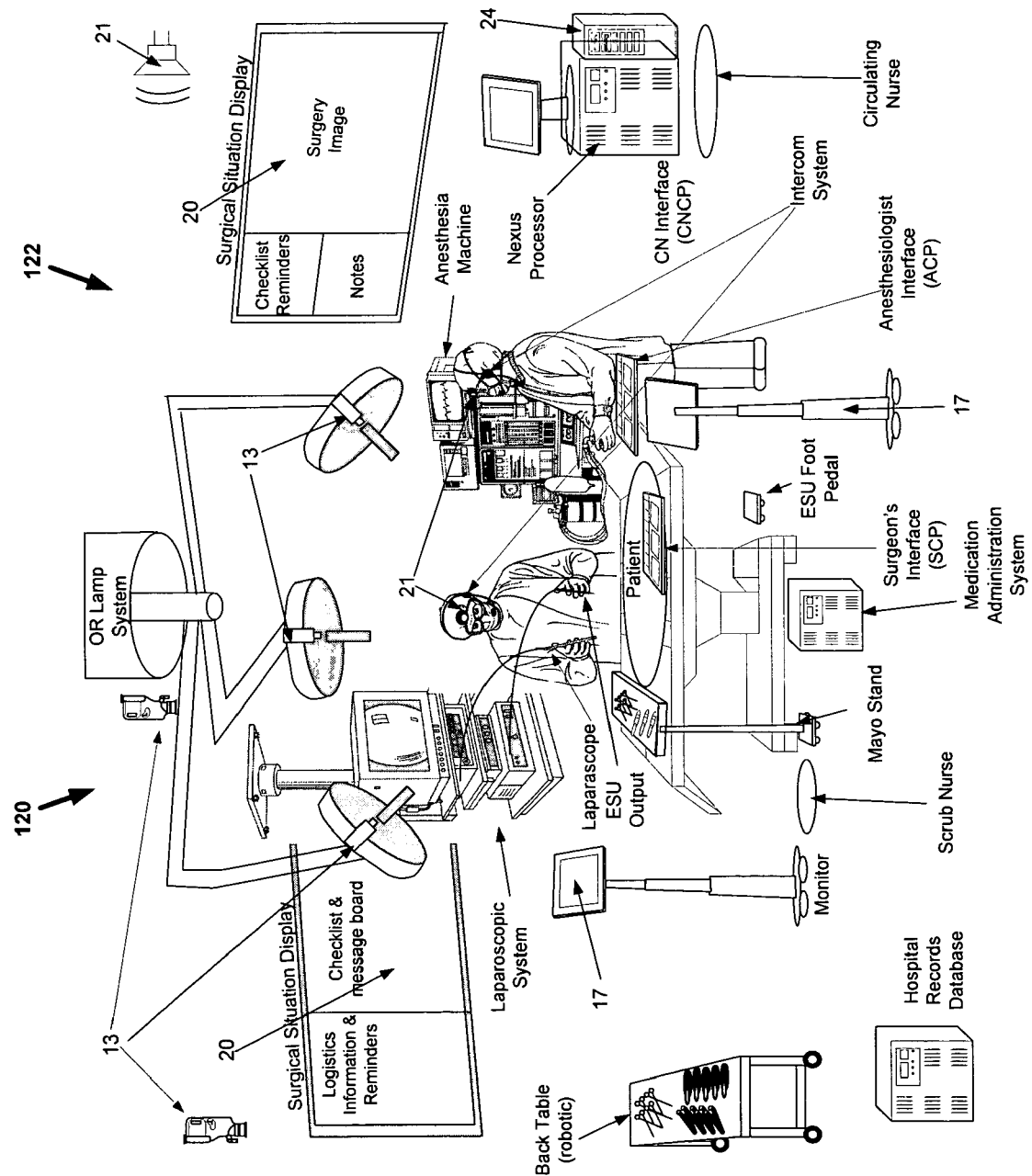
FIG. 3 is a schematic diagram showing some of the hardware subsystems of the interface shell, in accordance with an embodiment of the present invention.

FIG. 3 is a schematic diagram showing examples of the hardware subsystems 122 of the interface shell 120, in accordance with an embodiment of the present invention. Hardware subsystems 122 of the interface shell 120 include, but are not limited to, bar code sensors 10, radio frequency identification (RFID) sensors 11, localization sensors 12, digital video cameras 13, machine vision 14, intelligent tools (robots) 15, pushbuttons 16, touch panels 17, speech recognition systems 18, gesture recognition systems 19, large flat-panel displays 20, head-mounted displays 21, sound systems 22, wired and wireless data communication systems 23, and computer systems 24 required to process the data. The interface shell 120 obtains data from the hardware subsystems 122, communicates the data to the system agent 130 and function agent 140, and communicates information and commands from the function and system agents 130,140 back to the hardware subsystems 122.

Figure 4:
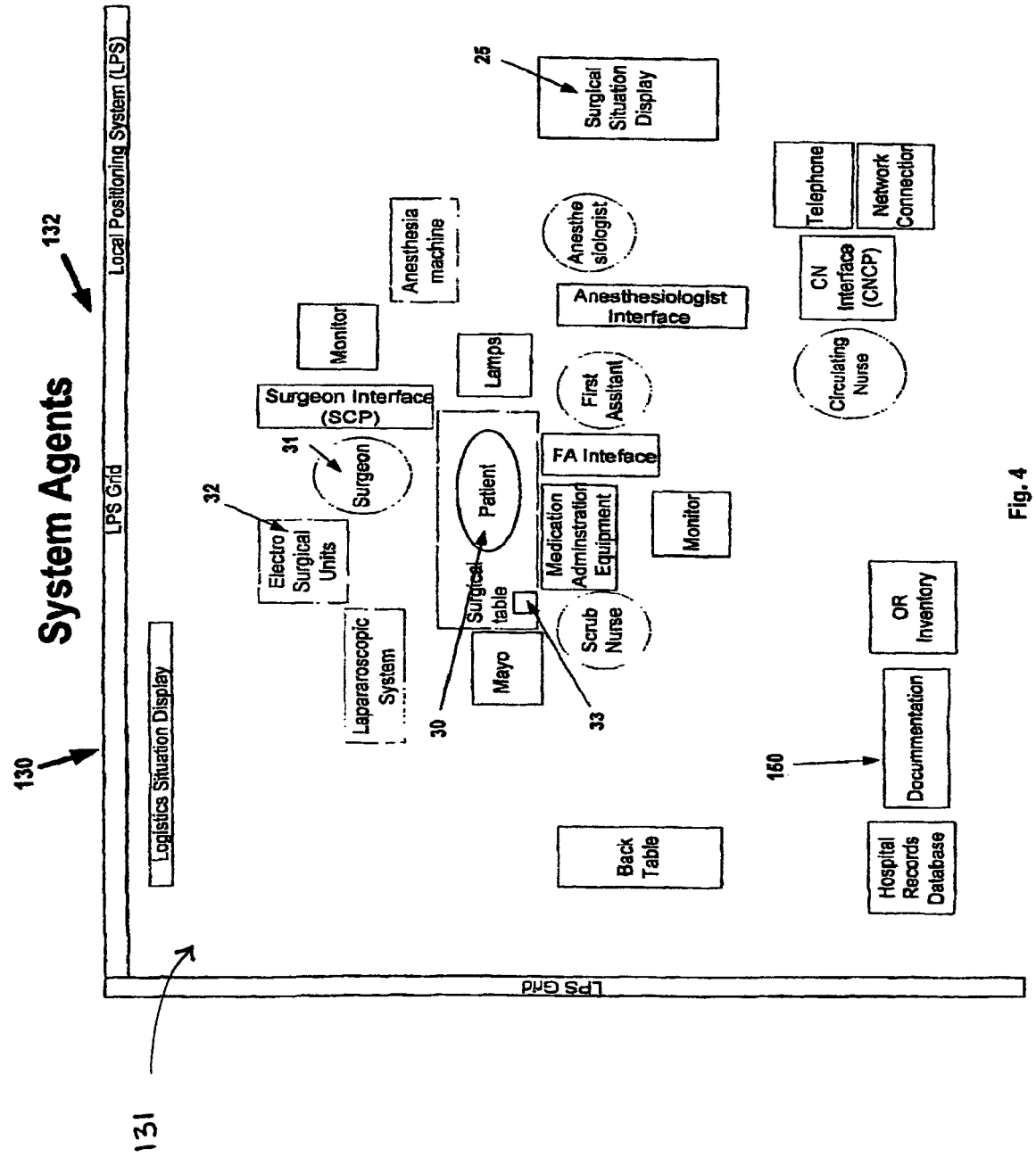
FIG. 4 is a schematic diagram showing some of the virtual elements, software representations, of the system agent, in accordance with an embodiment of the present invention.

FIG. 4 is a schematic diagram showing some of the virtual elements 132 (software representations) of the system agent 130, in accordance with an embodiment of the present invention. The system agent 130 comprises one or more system sub-agents 131 adapted to model and track the state of the OR. Every system, subsystem, and significant element of the OR, such as, but not limited to, the patient 30, the surgeon 31, the electro-surgery unit 32, a single sponge 33, has associated with it a dynamic, knowledge-based software object defined as a system sub-agent 131. The role of a system sub-agent 131 is as a liaison between the respective hardware subsystem 122 and the rest of smart system 100. The liaison roles include, but are not limited to:

maintaining a dynamic model of the hardware subsystem 122, including its structure (i.e., its subsystems and elements) and behavior (changes in state/status);

monitoring and tracking the state/status of the hardware subsystem 122, such as, but not limited to, the patient's blood pressure, the current settings of the electrosurgery unit 32, the physical location of a sponge 33;

anticipating the behavior of the hardware sub-system 122 by predicting its state/status into the future;

providing past, present, and projected hardware subsystem 122 state/status information to other system sub-agents 131 and the function agent 140;

alerting the function and system agents 130,140 and OR personnel to non-normal states of the hardware subsystem 122, such as, but not limited to, a sudden drop in the patient's blood pressure, or a drop in voltage in the electrosurgery unit 32;

relaying state/status information from other system sub-agents 131 to a hardware subsystem 122, such as, but not limited to, the patient's blood pressure to the surgeon 31 via a head-mounted display 21;

sending control information to the hardware subsystem 122, such as, but not limited to, new settings and on/off signals to the electrosurgery unit 32;

translating speech, such as, but not limited to, surgeon 31 comments, commands, and queries, to event and control codes recognizable by the smart system 100;

logging relevant time-stamped information such as, but not limited to, the patient's blood pressure, from the hardware subsystem 122 to a dynamic documentation file (DDF) 150;

performing diagnostics on its hardware subsystem 122;

sending data to the surgical situation display (SSD) 25; and warning personnel of potential problems with the hardware subsystem 122 via personnel agents.

In accordance with an embodiment of the present invention, a personnel agent, a type of system sub-agent 131, is adapted to, such as, but not limited to: use a knowledge base derived from a predetermined person, such as, but not limited to, a surgeon 31; relay individual-specific information to the predetermined person; translate speech to system-recognizable information, queries and commands; and log notes to the DDF 150.

Figure 5A:
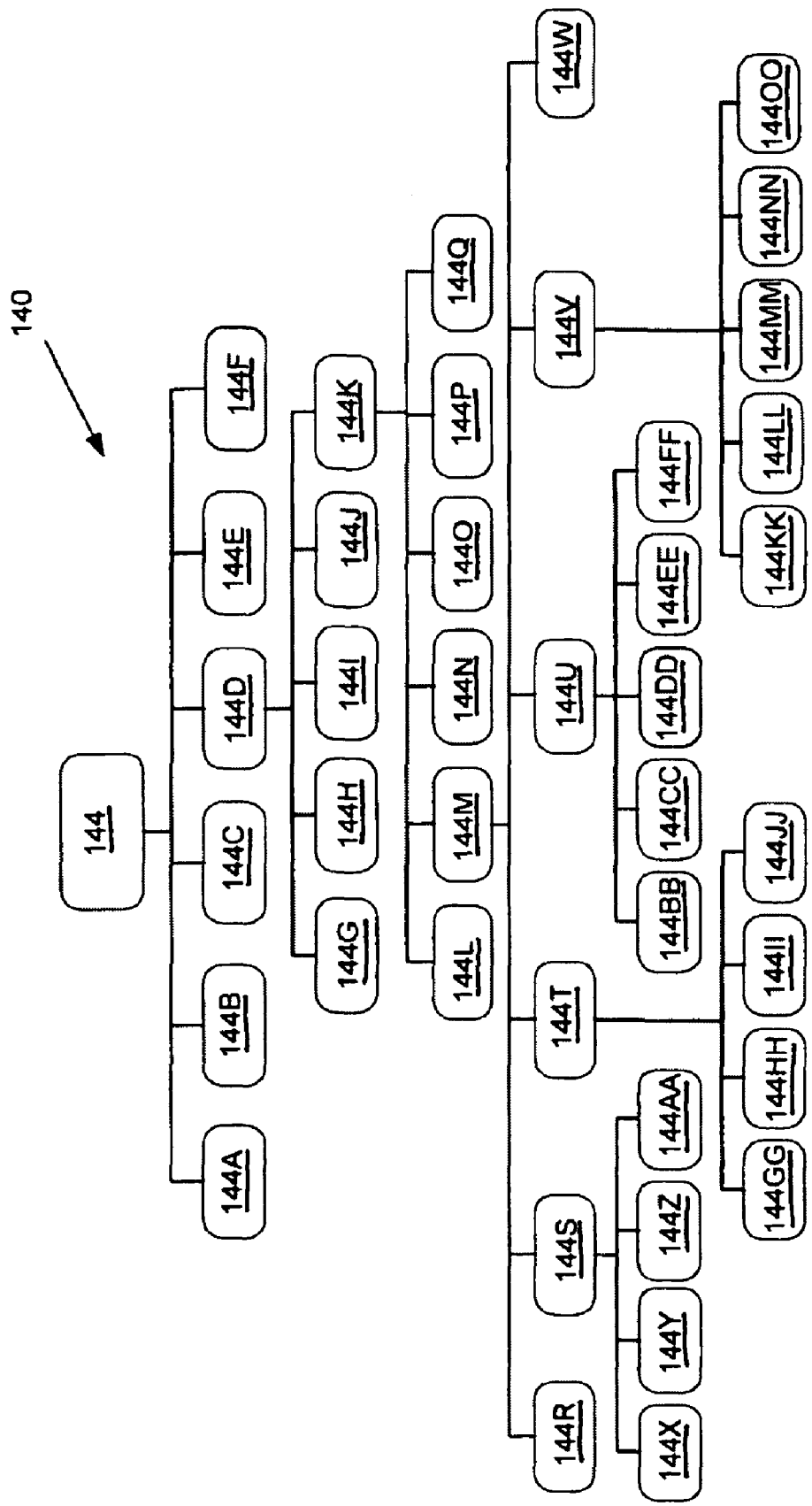
FIGS. 5A and 5B is a schematic diagram showing some of the elements of a function agent associated with performing laparoscopic surgery, in accordance with an embodiment of the present invention.

FIG. 5A is a schematic diagram showing an example of functions 144, 144A-144OO associated with a function agent 140 associated with performing laparoscopic surgery, in accordance with an embodiment of the present invention. The function agent 140 is adapted to model, track, and facilitate OR functions. A function is defined as a goal-directed process. By way of example, but not limited thereto, the process of surgery is represented as a hierarchy of functions 144, 144A-144OO and associated sub-function agents. The top of the hierarchy is the function 144 of a laparoscopic hysterectomy 144.

Figure 5B:
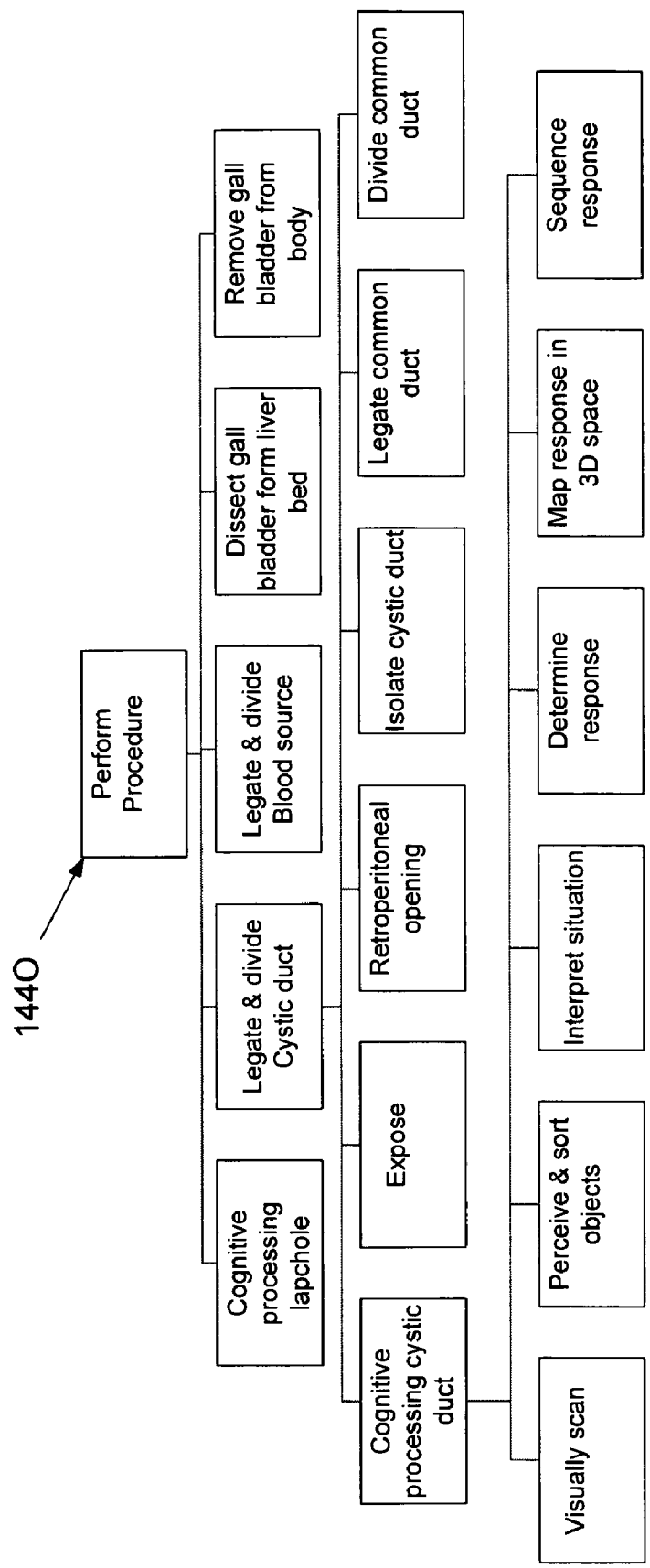

FIG. 5B is a schematic diagram continuing from the diagram of FIG. 5A. The functional agent extends beyond the periphery and into the heart of the procedure and in the embodiment this would be laparoscopic hysterectomy extending downward from function 144O the steps and sub-steps would form individual nodes and hence functional agents. Rules deriving from, such as, but not limited to, institutional policies, guidelines and professional organization guidelines and government regulations control these individual activities.

Each function 144 has associated with it a dynamic, knowledge-based object called a sub-function agent 244. The role of a sub-function agent 244 is to recognize when its function should begin, track the progress and status of the function, facilitate the performance of the function, and keep other system and function agents and personnel informed about the function.

Figure 6A:
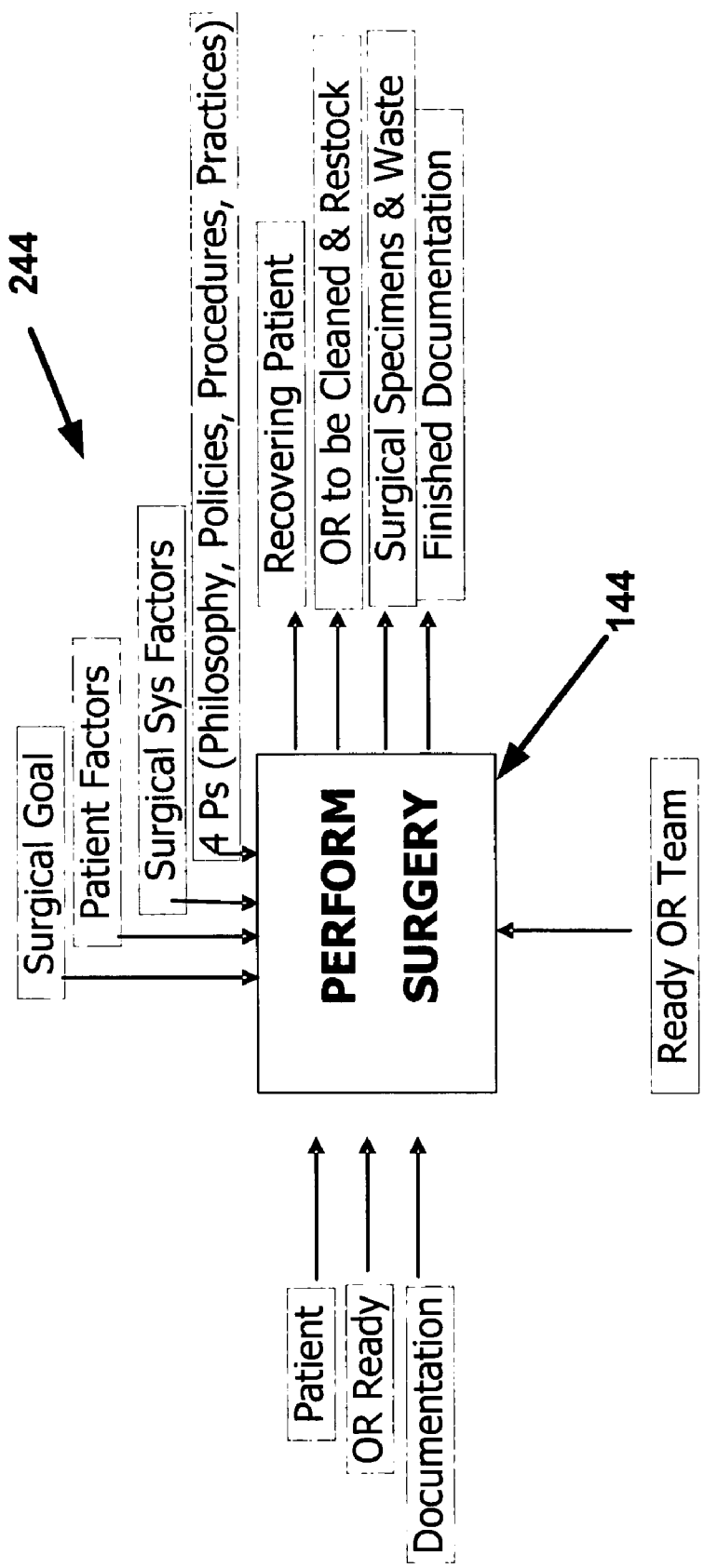

FIG. 6A is a schematic diagram of the underlying sub-function agent 244 associated with the laparoscopic hysterectomy function 144, in accordance with an embodiment of the present invention. The associated sub-function agent 244 comprises, such as, but not limited to, inputs, mechanisms, controls and outputs. The inputs are associated with the patient, readiness of the OR, and documentation. The mechanisms comprise the actors, such as humans and machines, which perform the function, among others. The controls comprise the goal and issues associated with facilitating or constraining the function, such as, but not limited to, the goal outcome, patient factors, surgical system factors, philosophy, policies, procedures and practices. The outputs comprise issues related to the result of the function, such as, but not limited to, the recovering patient, OR cleaning and restocking, surgical specimens and waste, and finished documentation.

Figure 6B:
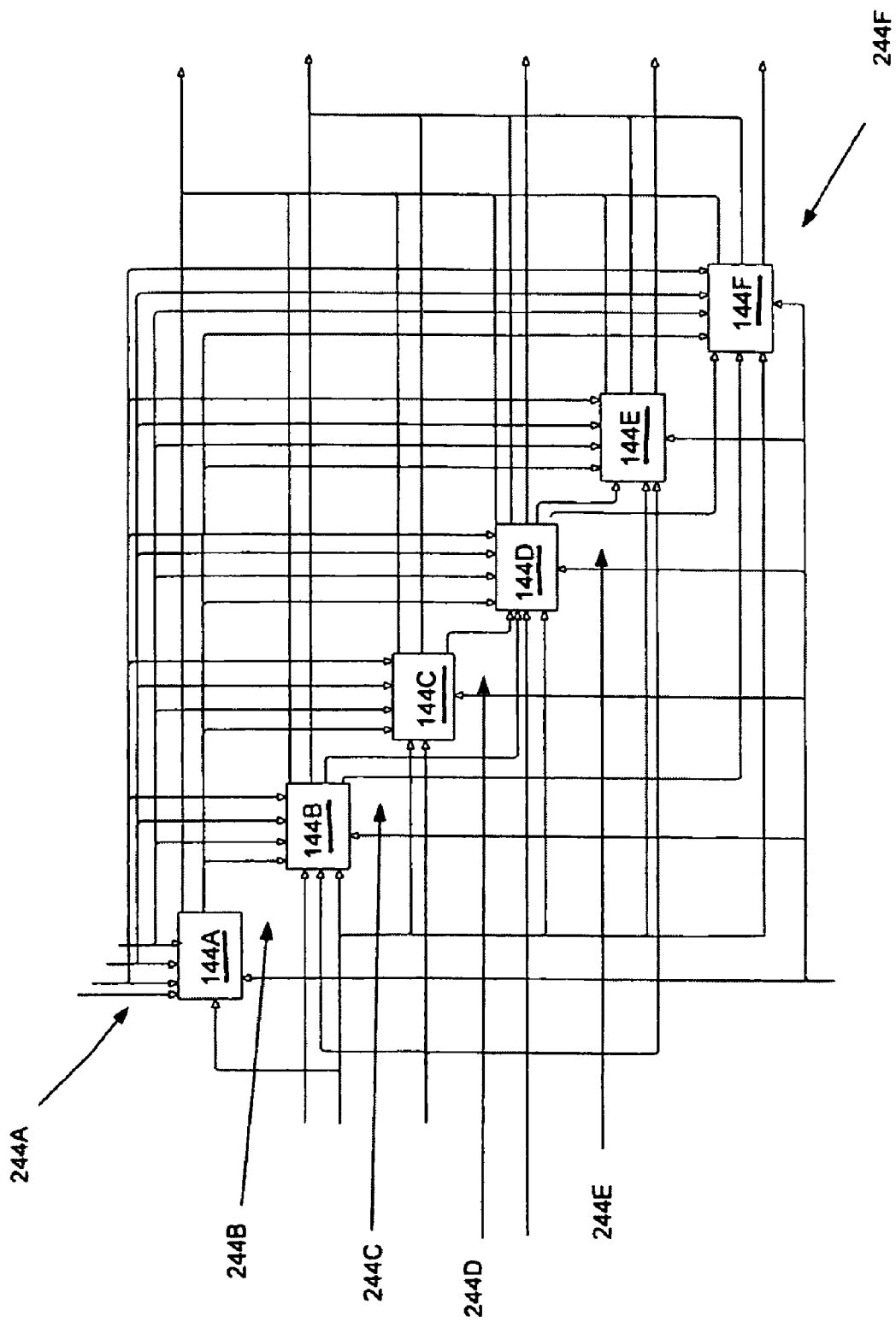

FIG. 6B is a schematic diagram of the underlying sub-function agents 244A, 244B, 244C, 244D, 244E, 244F extending from laparoscopic hysterectomy function 144 and associated with respective second level sub-functions: plan the surgery 144A, prepare the patient for the surgery 144B, prepare the OR for the surgery 144C, perform the surgery 144D, initiate patient recovery 144E, and restore surgical system to neutral state 144F, respectively as shown in FIG. 5A, in accordance with an embodiment of the present invention.

Figure 6C:
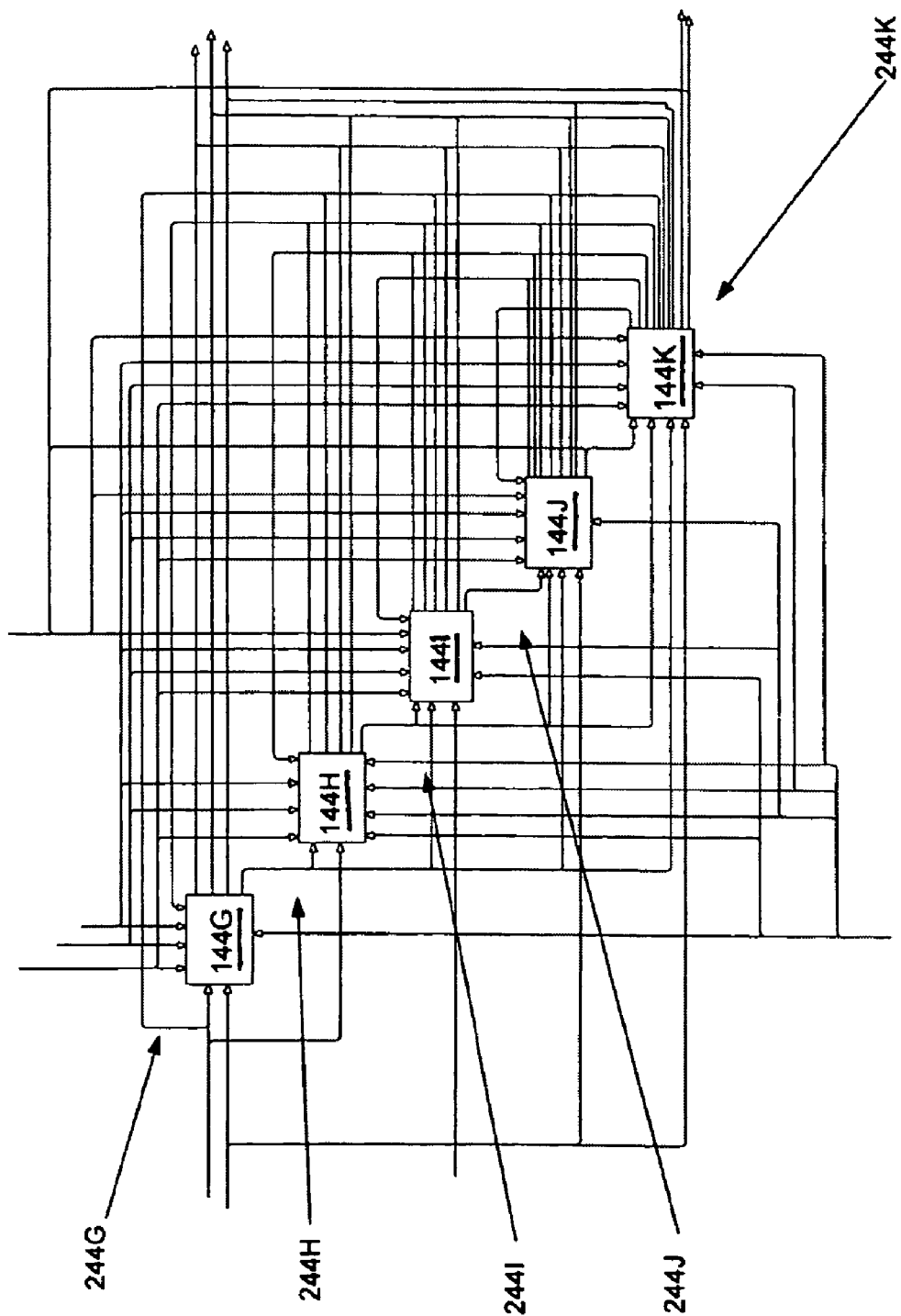

FIG. 6C is a schematic diagram of the underlying sub-function agents 244G, 244H, 244I, 244J, 244K extending from perform surgery function 144D, and associated with respective third level sub-functions: support OR functions 144G, configure OR 144H (including logistics support), manage patient position 144I, manage patient physiology 144J, and perform surgical procedure 144K, in accordance with an embodiment of the present invention.

Figure 6D:
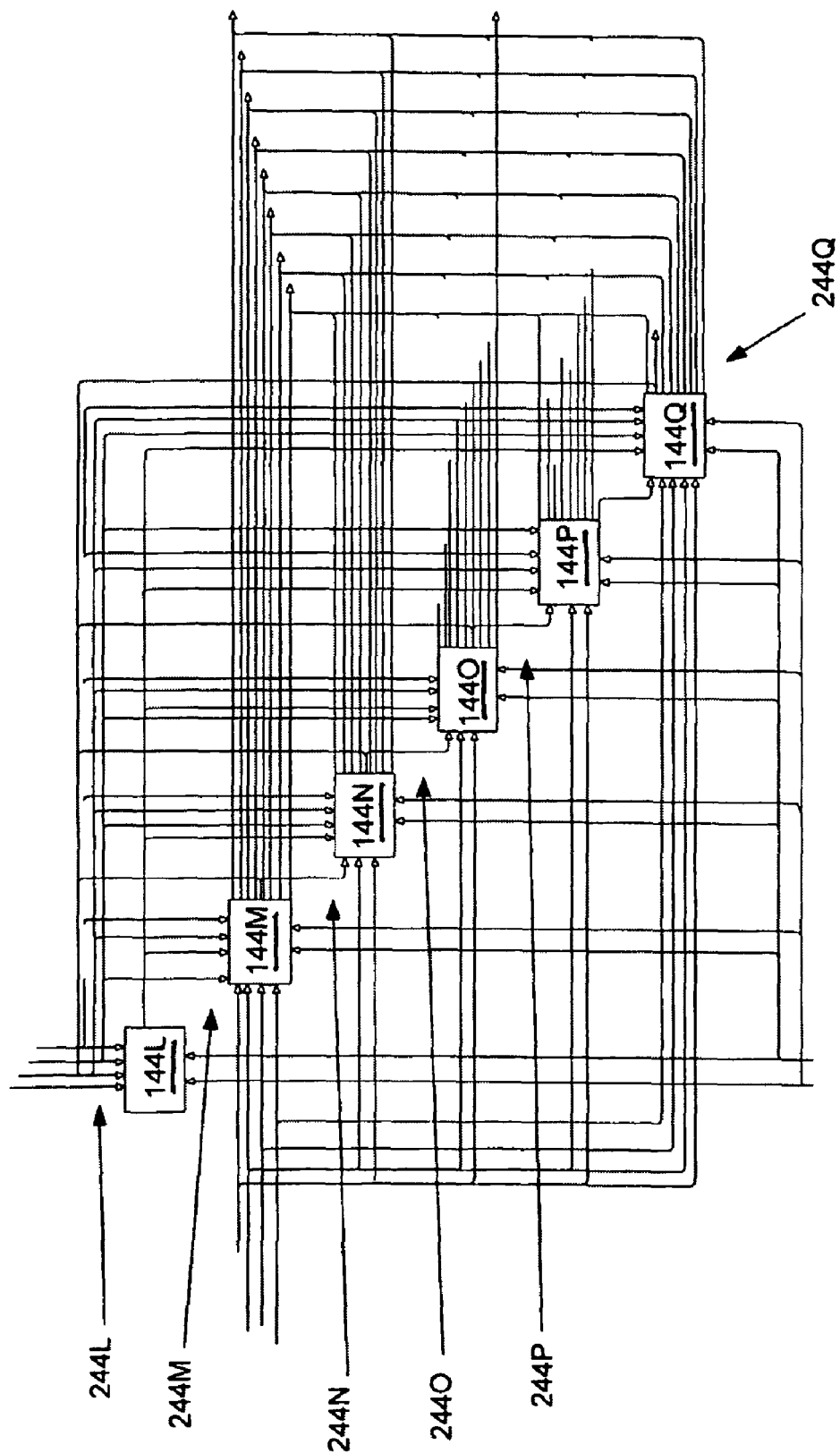

FIG. 6D is a schematic diagram of the underlying sub-function agents 244L, 244M, 244N, 244O, 244P, 244Q extending from perform surgical procedure function 144K: plan and assess 144L, create and maintain workspace 144M, prepare anatomic site 144N, perform procedure 144O, exit procedure site and region 144P, and close patient 144Q, in accordance with an embodiment of the present invention.

Figure 6E:
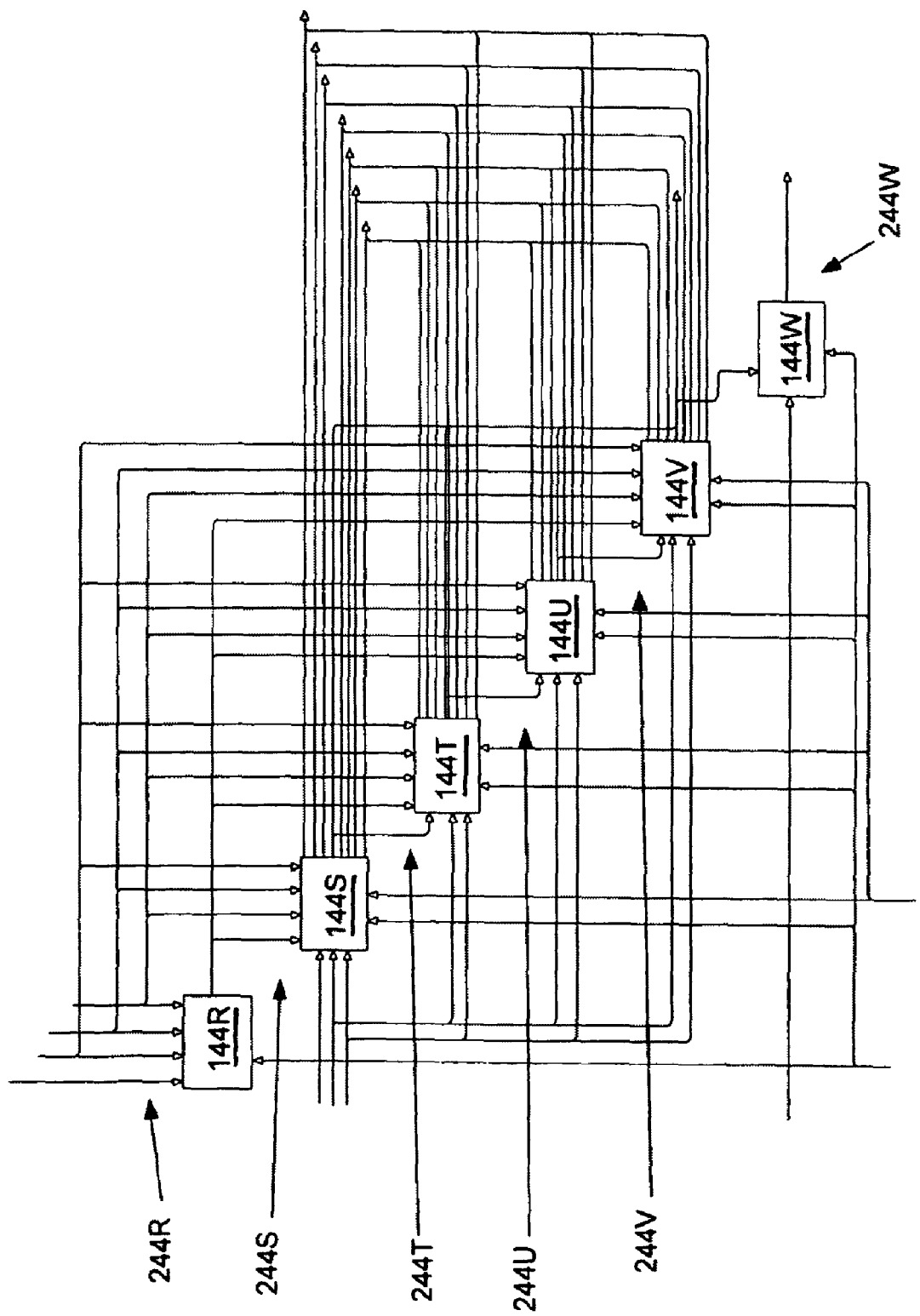

FIG. 6E is a schematic diagram of the underlying sub-function agents 244R, 244S, 244T, 244U, 244V, 244W extending from create and maintain workspace function 144M: plan and assess workspace 144R, insert and secure primary trocar 144S, insufflate abdomen 144T, insert and manage laparoscope 144U, insert secondary trocar 144V, and document workspace findings 144W, respectively, in accordance with an embodiment of the present invention.

Figure 6F:
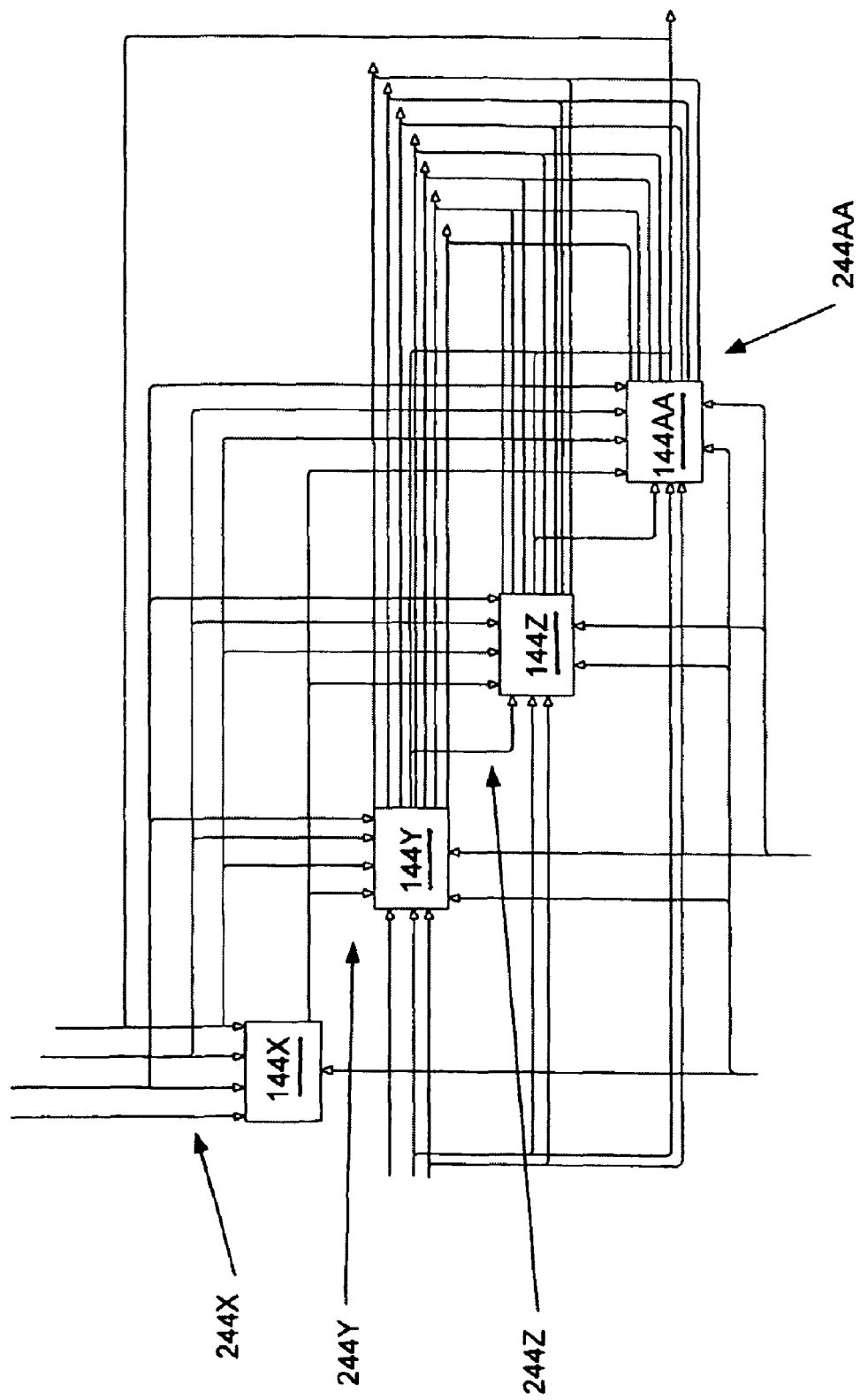

FIG. 6F is a schematic diagram of the underlying sub-function agents 244X, 244Y, 244Z, 244AA extending from insert and secure primary trocar function 144S: plan and assess primary trocar 144X, open abdominal wall for primary trocar 144Y, insert blunt trocar as primary 144Z, and secure trocar sleeve to abdominal wall 144AA, respectively, in accordance with an embodiment of the present invention.

Figure 6G:
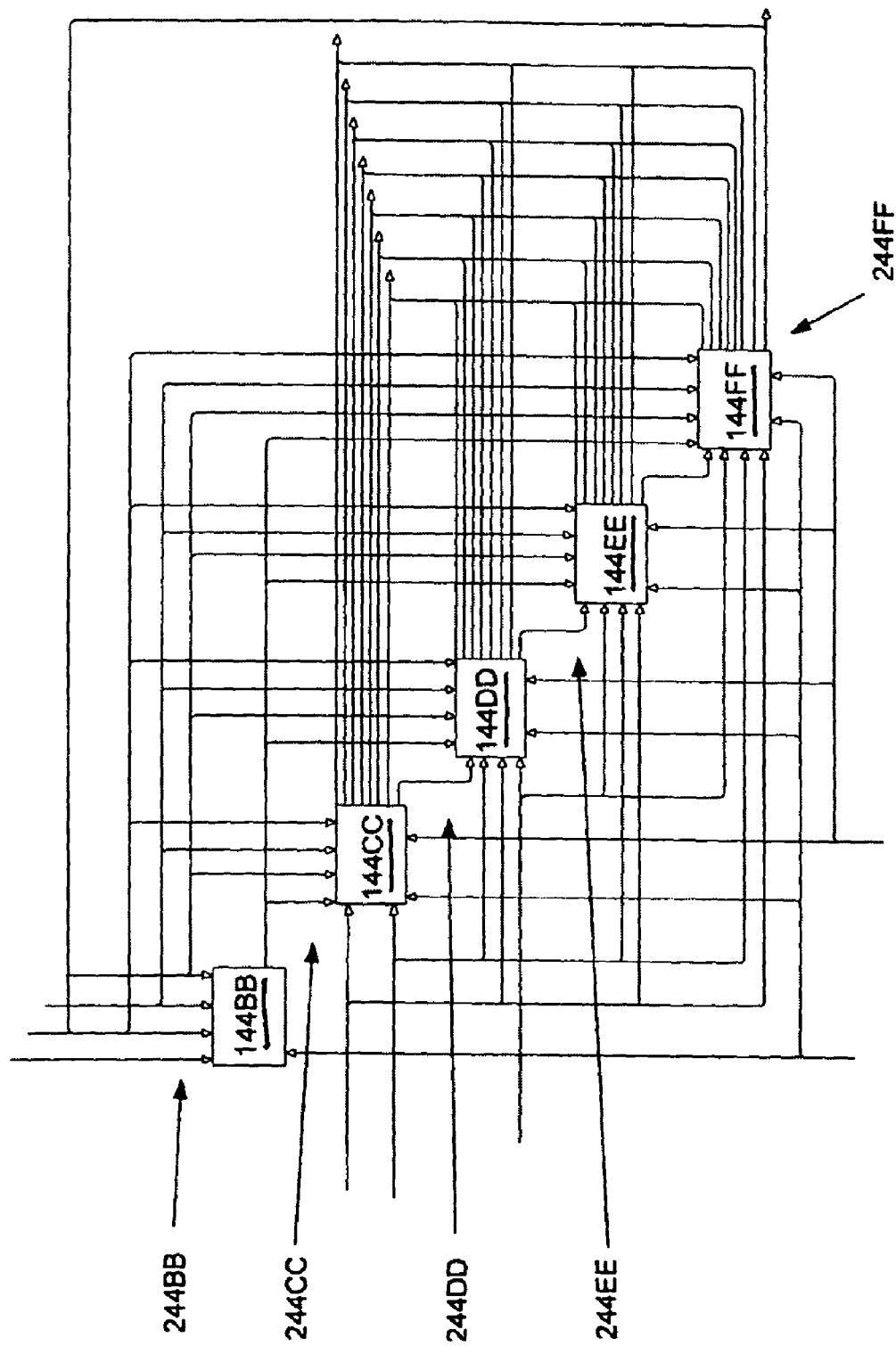

FIG. 6G is a schematic diagram of the underlying sub-function agents 244BB, 244CC, 244DD, 244EE, 244FF extending from insert and manage laparoscope function 144U: manage laparoscope 144B, connect light source and camera 144CC, insert laparoscope into trocar sleeve 144DD, orient camera 144EE, and maintain clear view of workspace 144FF, respectively, in accordance with an embodiment of the present invention.

Figure 6H:
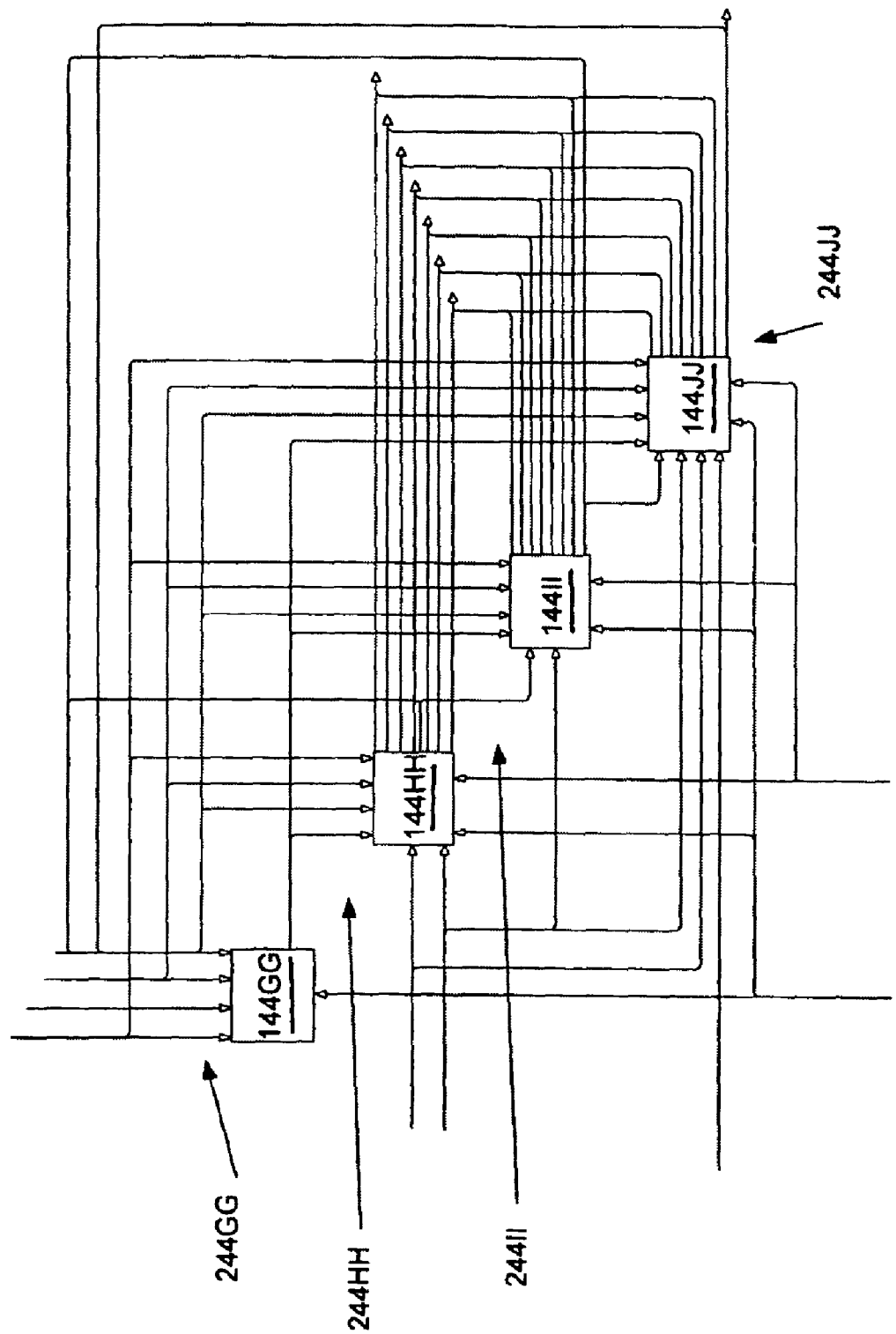

FIG. 6H is a schematic diagram of the underlying sub-function agents 244GG, 244HH, 244II, 244JJ extending from insufflate abdomen function 144T: plan and assess insufflation 144GG, secure tubing to trocar 144HH, control insufflator system 144II, and maintain internal space 144JJ, respectively, in accordance with an embodiment of the present invention.

FIG. 6I is a schematic diagram of the underlying sub-function agents 244KK, 244LL, 244MM, 244NN, 244OO extending from insert secondary trocar function 144V: plan and assess secondary trocar 144KK, prepare secondary trocar 144LL, select sites for secondary trocar 144MM, incision for secondary trocar 144NN, and insert secondary trocar 144OO, respectively, in accordance with an embodiment of the present invention.

The function agent 140 is adapted to, such as, but not limited to:

maintain a model of each sub-function agent, including its state (including pending, active, suspended, completed), stage, including to what extent the function has been completed and its goal is accomplished, and status, including satisfactory, marginal, unsatisfactory;

maintain procedural knowledge about the function, including the major steps in the procedure;

monitor all OR subsystems and elements relevant to the function via the respective system sub-agents;

know and determine when its function should be initiated;

cue personnel, via the respective system sub-agents, when its function is nearly ready to begin;

track the progress and performance of its function;

provide appropriate procedural cues to personnel, when needed;

determine what information is needed to complete the function and make it available;

provide decision support and recommendations, if requested;

recognize potential errors and inform personnel;

recognize when the function's progress and/or performance is unsatisfactory and inform personnel;

recognize when the function is completed;

log significant procedural events and other information to a documentation file;

resolve conflicts among subordinate function sub-agents;

monitor speech via respective system sub-agents;

log events to the DDF 150, including, but limited to, text and images;

send filtered information to the SSD 25; and resolve conflicts among sub-function agents using prioritization rules.

The decision making process and activities involved in performing a surgical procedure contain complexity and subtlety that have long resisted reduction to a simple model of what occurs within an operation. Integrated Definition (IDEF) modeling captures the complexity of the task interrelationships and decision making, thereby allowing one to approach surgery at the appropriate analytical level for the individual steps involved in a surgical procedure.

IDEF is a group of modeling methods that can be used to describe operations in an enterprise. Currently, sixteen methods, from IDEF0 to IDEF14, including IDEFIX, are each designed to capture a particular type of information through modeling processes. For example, IDEF0 methods are used to model the functions of an enterprise, creating a graphical model that shows what controls the function, who performs the function, what resources are used in carrying out the function, what the function produces, and what relationships the function has to other functions.

Unified Modeling Language (UML) is another approach used to model real-world objects. UML specifies how to describe: the class of object, the object, association, responsibility, activity, interface, use case, package, sequence, collaboration, and state.

Smart system 100 functions are based on an expandable model of the surgery which integrates the declarative knowledge contained in surgical atlases, journals and texts into the computer code that guides the OR team and equipment through the central process and concurrent parallel activities within the OR. Construction of a functional model of the OR using appropriate engineering tools provides the needed framework of for analysis and refinement of the central surgical process. The model will have the flexibility to follow the processes of an operation or set of operations as the surgeon elects to change the usual sequence of procedures or steps within a given procedure.

Process support does not limit the surgeon to a rigid script but rather follows the surgeon-directed flow of the procedure and insures that all of the loose ends come together neatly by the conclusion of the operation.

A process is provided below by way of example, but not limited thereto, as to the function of smart system 100, as applied to a surgeon attempting to clamp a blood vessel during a laparoscopic surgical procedure. The surgeon verbally requests a "medium microclip". A speech recognition system associated with the surgeon interprets the surgeon's speech. A surgeon system sub-agent encodes the speech and communicates it to other agents. A control hemorrhaging function sub-agent recognizes the surgeon's intent as consistent with correct procedure. A scrub nurse mistakenly hands a small microclip tool to the surgeon who does not notice the error. An overhead camera tracks a small microclip tool from a Mayo table to the sterile field and communicates data to a small microclip tool system sub-agent. The small microclip tool system sub-agent communicates its position in the sterile field to the control hemorrhaging function sub-agent. The control hemorrhaging function sub-agent recognizes the discrepancy and informs the surgeon via the surgeon system sub-agent and a surgeon's head-mounted display. The surgeon returns the small microclip tool to the scrub nurse.

Structural and functional models of the OR for respective forms of surgery are created and implemented in smart system 100. A system hierarchy model of the structural elements of the OR system and an IDEF0 functional model, for example, is created. The models are revised and expanded based on the experience and expertise the physicians on the team and with the help of other subject matter experts such as physicians, nurses, and technicians.

From the system hierarchy model, a set of sensor, actuator, and communication systems necessary to implement smart system 100 functionality is identified. Component and interface specifications for the acquisition and integration of the physical components are identified.

From the system hierarchy model, the IDEF0 functional model software specifications are created. The specification may be presented in, but not limited to, Unified Modeling Language (UML), Use Case, Class Object, Activity, and State chart diagrams. A model based knowledge base is utilized to construct the hierarchy and operations.

Figure 7:
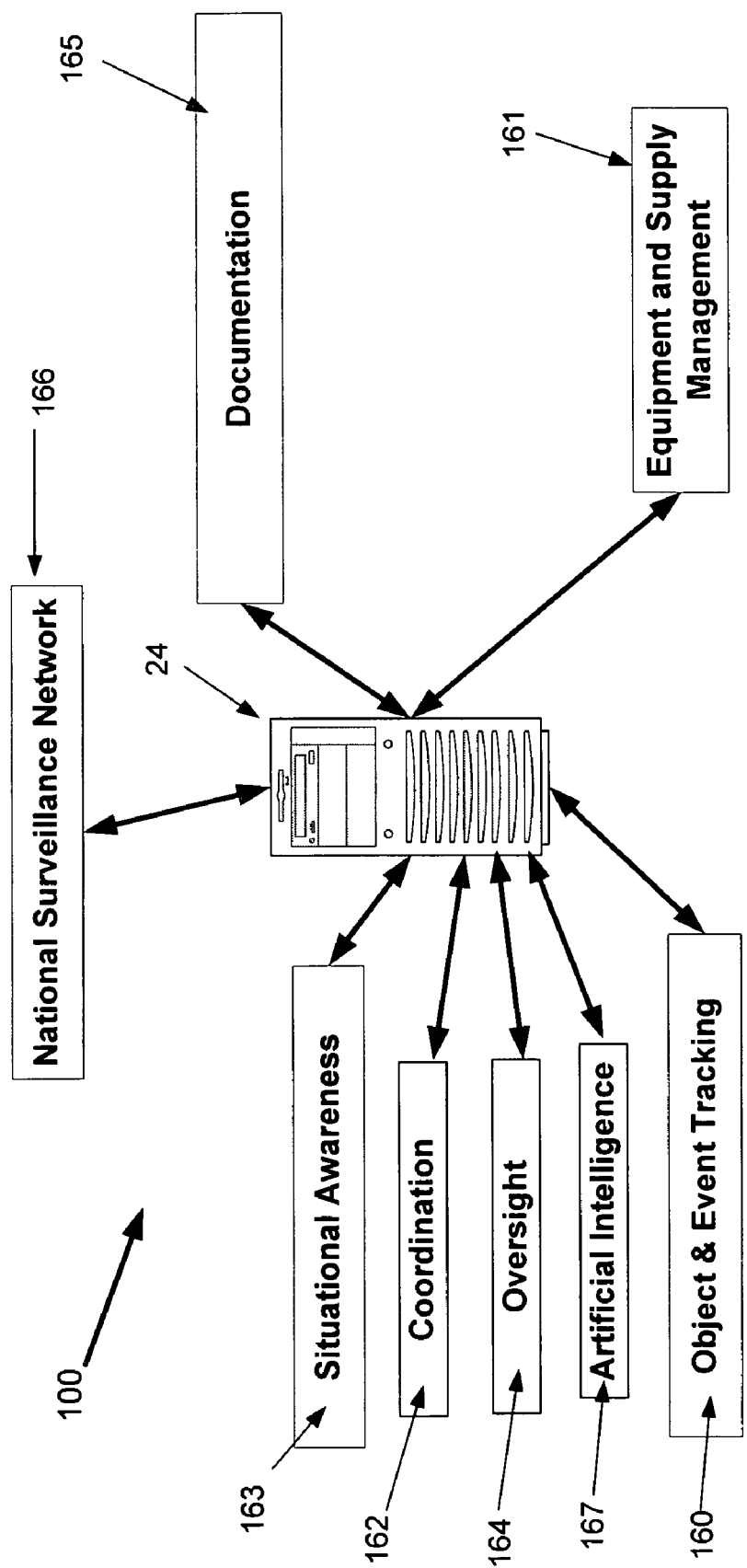
FIG. 7 is a schematic diagram showing some of the elements of the layering architecture, in accordance with an embodiment of the present invention.

FIG. 7 is a schematic diagram showing some of the elements of the layering architecture, in accordance with an embodiment of the present invention. The smart system 100 achieves practicality through a layering architecture that starts from the most basic functions to the most complex. In embodiments of the smart system 100, layers include, but are not limited to: tracking layer 160; equipment and supply management layer 161; coordination layer 162; situational awareness layer 163; oversight layer 164; documentation layer 165; national surgical surveillance network layer 166; and artificial intelligence layer 167, interconnected by a computer system 24.

Each of these layers is of increasing complexity and relies on the underlying layer(s) to complete their functions. The tracking layer 160 is a superset of the system agents 130. The tracking layer 160 tracks the instruments, equipment and expendables, as well as, but not limited to, the personnel, such as the surgeon, anesthesiologist, and patient. The tracking layer 160 relies on varied technologies including, but not limited to, bar coding, machine vision, EMFM transponder schemes, and LED beacon tracking systems within the OR.

The equipment and supply management layer 161 is the layer that is interactive, in that it takes the information from the tracking layer 160 and then processes that in regards to, among other things, the hospital records and inventory and maintenance systems for the entirety of the OR equipment and expendables.

The coordination layer 162 coordinates the myriad of data features from the tracking layer 160 and the equipment and supply management layer 161 to develop an image of what is occurring in comparison to what the overall plan is based on relevant predetermined surgical models. Within the coordination layer 162, the majority of the function agents 140 are collected. The coordination layer 162, with the equipment and supply management layer 161 and tracking layer 160, makes the broad base of the pyramid upon which more subtle and complex functions and data manipulation can occur.

The situational awareness layer 163 is where the surgical displays and the output features of the various interfaces, including the surgical workstations, reside, among other things. This is the first level of human-to-smart system 100 interaction. The situational awareness layer 163 provides decision support to the human actors by accessing the knowledge base, among other things, and communicates the appropriate data in the knowledge base to the human actors.

The oversight layer 164 combines the developing situation information and the situational awareness with the function agents 140 so that smart system 100 can determine if the processes are being preformed correctly and if there are any developing dangerous situations. The oversight layer 164 generates warnings and cues, among other things. Other items within the oversight layer 164 include, but not limited to, checklist data for human actor verification of key events within a given surgical plan. The oversight layer 164 contains the virtual mirror for the human team to examine their actions and activities in relationship to the ideal goals.

The documentation layer 165 takes the immense stream of data from the other layers 160, 161, 162, 163, 164 and organizes that information into reports for standard surgical documentation and/or provides data points that are used for surgical research on a national network basis, among other things.

The national surgical surveillance network 166 is a network of a plurality of systems 100 in communication to mine the documentation data and look for vulnerabilities, areas for improvement, increased effectiveness and efficiency.

The artificial intelligence layer 167 characterizes the patterns of smart system 100 as a macro network construct from all the data. This is a method of augmenting human analysis of the data and this information can stream downward toward the surveillance layer 166, documentation layer 165, and oversight layer 164, and then to the fundamental programming of the smart system 100 and network as a whole.

Looking into each layer, it is appreciated that there are software agents contained at the appropriate level of layers. Multiple threads of data and process data link these agents together. Substantially all of the operations and interrelationships of the OR are provided by smart system 100.

From one smart system 100 to another smart system 100, a standard protocol is utilized to ensure that documentation, tracking protocols, and processes are uniform throughout the systems 100. This enables effective interjection of artificial intelligence at the layer of national surgical surveillance network 166.

Figure 8:
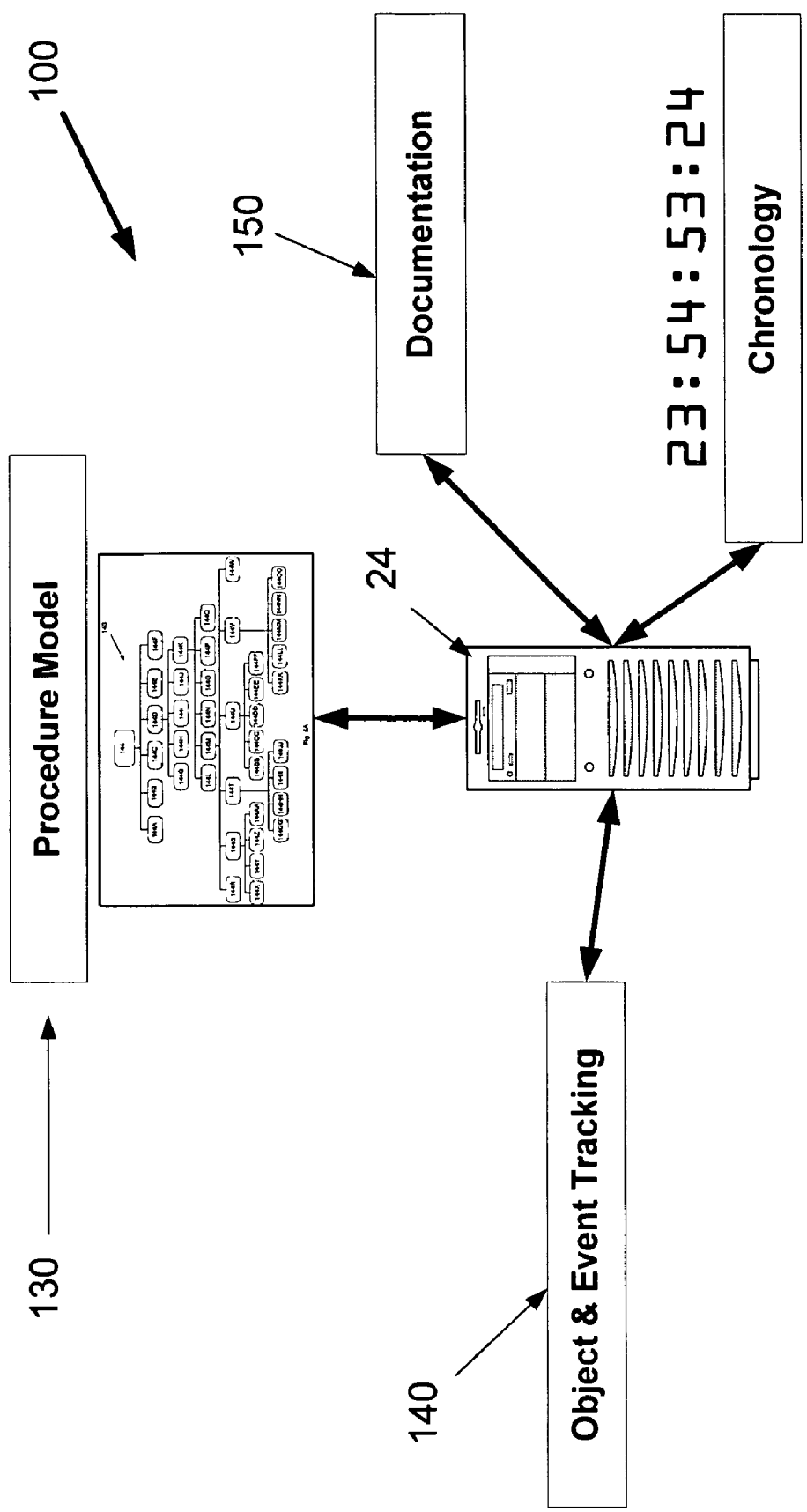
FIG. 8 is a schematic diagram of a dynamic documentation system in accordance with the present invention.

FIG. 8 is a schematic diagram of a dynamic documentation system (DDS) 150 in accordance with an embodiment of the present invention. The smart system 100 comprises the DDS 150 linked to the function agents 140 and system agents 130 by way of the computer system 24. Documented tasks include, but are not limited to: adherence to basic standards; cataloging significant peri- and intra-operative events; accurate billing; establishing a medical legal record; and research data.

In embodiments of the present invention, sensors are adapted to provide an automatic, accurate method to collect information with a minimum of human interaction in order to populate the OR database in real time. The sensors are used, among other things, to track material flow, activities and central processes occurring in the OR in real-time.

By way of example, but not limited thereto, sensors include video and audio sensors. These sensors are adapted to provide real-time photos and video documentation to track rapidly evolving events. This data enhances and strengthens the record, and ensures accurate recall on the part of human actors. Smart system 100 creates a surgical record.

Using modeling, such as, but not limited to, IDEF0-defined milestones of a respective surgical procedure, the video and audio sensor and equipment performance data is "tabbed" and archived into a master procedural record, allowing for rapid identification and playback. The data is also stamped chronologically so that time, motion and function are captured and the data can be collated accordingly.

In an embodiment in accordance with the present invention, dynamic documentation tabbing involves extemporaneous acknowledgement of the surgical team to agreed-upon milestone events, such as, but not limited to, opening the abdomen, and taking a sponge count. The event enters the record as it occurs, correlating to the video and master data record. The documentation has XML or other appropriate mark up language, sub points, which are determined by system analysis as to major milestones within the surgical procedure, sensor data, and items of demonstrated vulnerability to error, among others. The video frames, speech and other portions of the overall data stream are tagged with multiple XML labels that allow smart system 100 to browse the data.

The OR process record is provided to determine adherence to best technique/quality models for the operation being preformed. The video systems and machine vision, coupled with enhanced playback and editing, is provided to help the surgeon recreate events within the OR for error correction. For example, but not limited thereto, a query is performed, such as, but not limited to, as to the location of a lost sponge or what the initial color and the texture of an organ or tissue prior to the completion of surgery.

XML tagging methods are known in the art of computer information systems.

A logical division of records is provided and adapted for analysis. Verbal commentary from the surgeon and open microphone comments from each OR participant is stored in a corresponding audio log. Voice recognition is provided so that a respective OR participant is recorded into the patient record tagged with the identification of the source. The surgeon and other team members dictate intentions, findings, or problems, among other things, into the record. The verbal actor inputs not only record events, but also provides aids for navigating through the procedure. Combined with keyboard inputs and updates, the verbal record creates an information rich record that captures the actors' situational awareness and decision process. The physical activities of surgery, such as the movement of specific instruments which are tagged, such as, but not limited to, by barcode and/or RFID, indicate key milestones in the procedure provide XML punctuation points for the video record indicating where the surgical team is in the surgical process.

Figure 9:
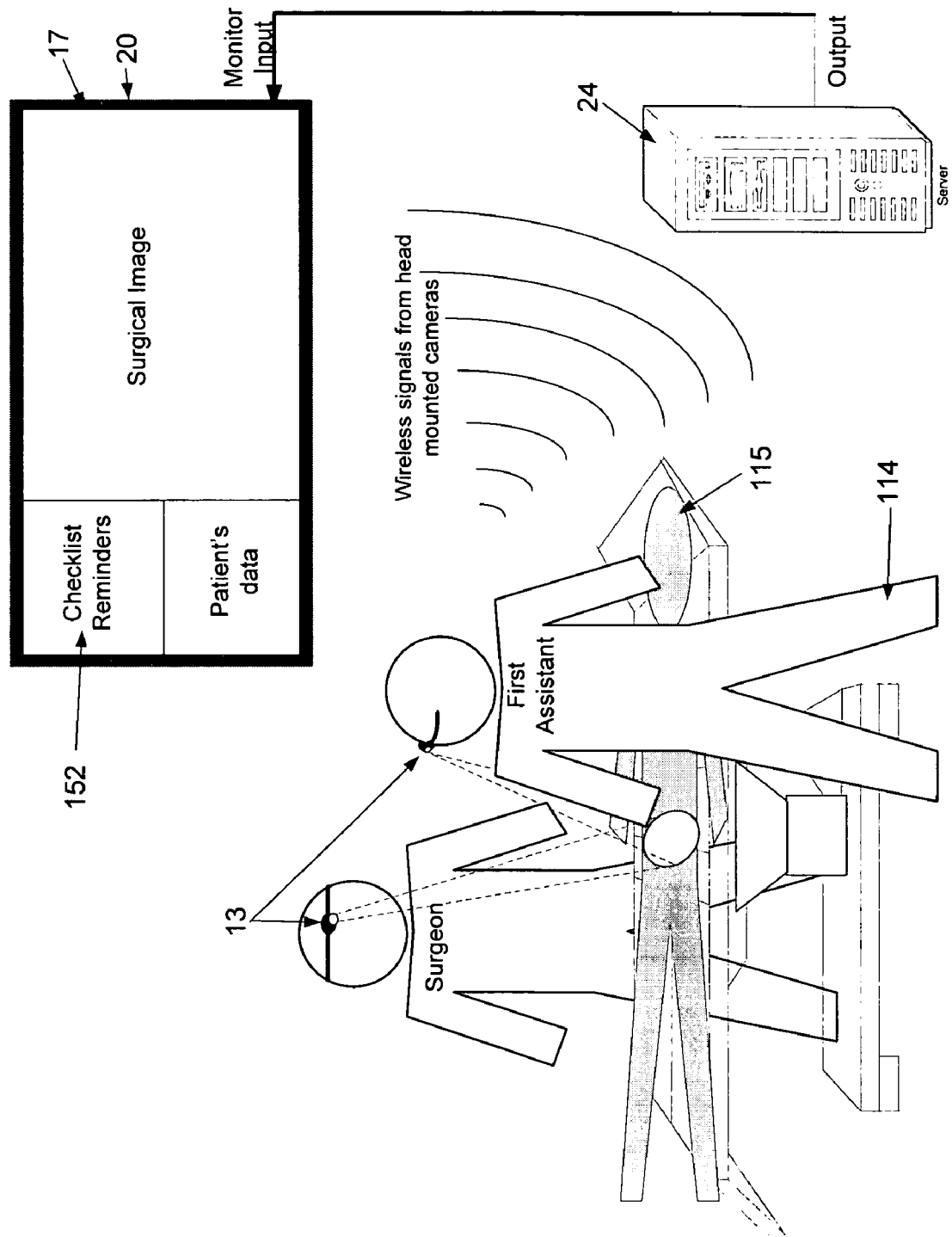
FIG. 9 is a schematic diagram of a checklist system in accordance with the present invention.

FIG. 9 is a schematic diagram of a checklist system 152 in accordance with the present invention. Checklists are provided to the OR actors. Each surgical procedure has certain steps, methods and specific checks to insure surgical quality and patient safety. A checklist based on current practice distills down the items found to be essential as defined by the texts, professional guidelines, standard operating procedures and the primary items for best practice is provided. Smart system 100 monitors in real-time clear thought verification and definitive observed action throughout the process. Each element of the operation has its own checklist items that dovetail into a master checklist instilled into smart system 100.

Checklist information is prioritized according to the urgency or priority of actions. In one embodiment in accordance with the present invention, information is provided by monitors installed in the OR with which the user can navigate quickly through screens to locate information, such aw by touch and voice command, among others. Personnel can find the best practice of a respective procedure, be it caused by anticipated or unanticipated events or conditions.

Dynamic documentation increases situational awareness on the part of OR team members. The inclusion of voice recognition and specific workstation input identifies the human actors and holds them responsible for the accuracy and effort to accomplish the checklist-prescribed event. The process meshes smoothly with the team members' activities, as well the overall activity in the OR. Intelligent prompts are conveniently packaged in the form of both predescribed inputs through a checklist, and the checklist can, in an embodiment, be projected on a flat screen monitor providing situational and logistics information as well, to which the OR team can view and respond. The end result is increased team member alertness, vigilance and orientation during the surgical process.

The checklist content is predetermined by recognized standards defined by governmental agencies, professional organization, textbooks, and standard practice. While the hospital and individual surgeon can include local items, the inclusion of standards of practice will insure a basic level of quality if the checklist is followed.

The smart system 100, by way of the DDS 150 of FIG. 8, prompts the actors for input throughout the procedure, in accordance with an embodiment of the present invention. In addition to "yes" (affirmative) or "no" (negative) responses, some prompts require the specific actor(s) to search out the information and verbalize the data, such as, but not limited to, the "O2 saturation is 98% after intubation"; "sponge count is 26" or "a strong pulse is felt below the vascular graft". Other prompts are provided to initiate free thought, for example: "Is there anything we could be doing now"; "do you anticipate any problems with the way things are going"; and "do you have any suggestions to improve things"? In this way, utterances are recorded contemporaneously with the event, capturing and recording for future evaluation and consideration.

Another human attention enhancing device is gaming, where the actor knows that an error is present and is rewarded for finding it. These devices will increase human alertness and help the OR crew be mentally nimble and focused.

Figure 10:
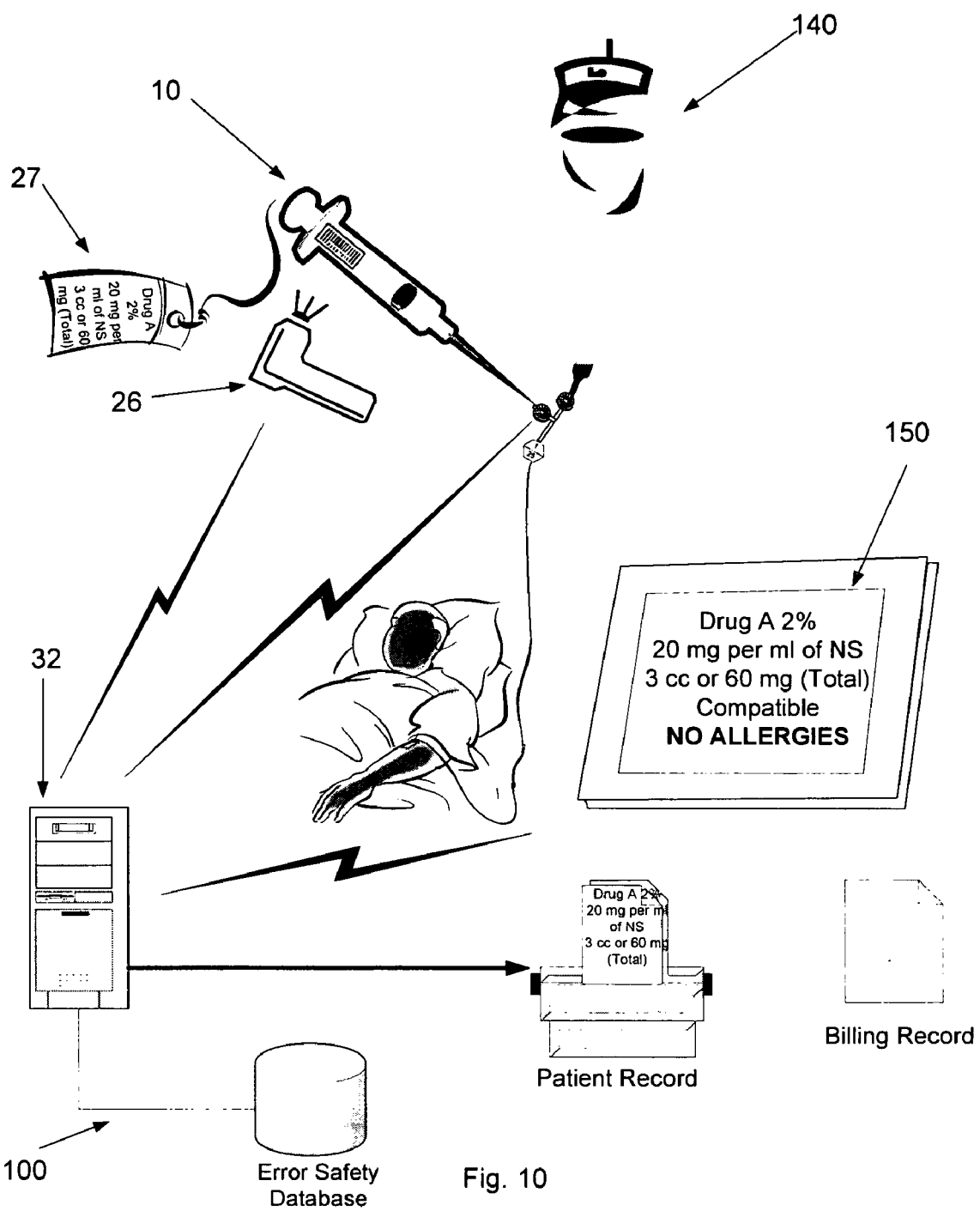
FIG. 10 is a schematic diagram showing some of the elements of the dynamic documentation system integrated with functional agents, in accordance with an embodiment of the present invention.

FIG. 10 is a schematic diagram showing some of the elements of the dynamic documentation system 150 integrated with functional agents 140, in accordance with an embodiment of the present invention. The dynamic documentation system 150 integrated with functional agents 140 has enough forethought to track surgical events and anticipate the next likely step. The dynamic documentation system 150 cues the operator and team members.

The following is presented by way of example, but is not limited thereto, as an application of the dynamic documentation system 150. All of the injectable and oral medications are marked with barcodes 10 as well as conventional labels 27. Barcodes 10 are referenced as each step in the process for automated tracking and elimination of confusion. A second barcode reader is built in to the IV pump, as well as an LCD display screen. The barcode reader verifies the identity and dose of the injectable drug. System 100 cross-checks patient allergies, prescribes a dosing schedule, and offers drug cross-reactions and special considerations. As the syringe goes into the port, the barcode information is captured, allowing smart system 100 to make the necessary checks and project information onto the screen in ready view of the nurse or physician. The medication name flashes on the screen, along with the amount, dosage, concentration, and other information as appropriate. These prompts serve as a ready check for the provider, insuring correctness of the intended action.

If for example the anesthesiologist intends to give drug "A" but has forgotten the patient allergy history, smart system 100 would flash a warning giving the doctor a chance to correct the error. An electronic stopcock would then close preventing drug administration. The event would be documented and captured. The warnings could be overridden with a voice command and the safety stop reversed if the physician or nurse determines the drug must be administered despite the possible risks.

Smart system 100 makes the operator take time to reconsider and confirm actions. Events are documented as they occur. Using electronic instrumentation, either in the syringe, IV line, or other surgical instrumentation, the exact dosage of medications, the power settings, among others, can be put into the record exactly at the time the event occurs. In this manner, there would be master logs of the events and administration of drugs. This log would then be altered with verbal or typewritten updates as to the part of the procedure that was occurring so that the entire context of the different activities is preserved. The dynamic documentation process will free the OR personnel from much of the paperwork they are plagued with, allowing concentration on direct surgical support.

Each human actor in the OR must have access to the pertinent information in order to understand the "OR systems." Information must be given at an appropriate level for them to intelligently function above the level of reflex reaction. The actors must be aware of the "state" of things within the OR, such as, but not limited to, the patient and the equipment instruments. Defining the current "state" of an object does not have full meaning in itself and alone would be an imperfect fragment of information. Temporal context is required and state information is framed in the past, present, and future predictions. State information is contained in the individual system agent.

The state of the patient, captured by the patient system agent, can be defined as the aggregate of, but not limited to: clinical history; physical exam findings; current laboratory and radiology findings; and current physiological state of the patient. Clinical history includes identifying data, medical history, allergies, medications, and family history, among other things. The clinical history database follows the standard framework of medical history format currently taught in medical and nursing schools: history of present illness, including current working diagnosis, differential diagnoses and symptoms; past medical history, including actively treated diagnoses, inactive diagnoses, treating or managing physicians for each listed diagnosis; past surgical history; allergies, including allergenic substance, and associated types of reaction; usual medications, dosage and administration instructions, prescribing physician, date began, degree of patient compliance, time and date of last dose, intended medical condition for each medication; and family history, including type of disease, relative with disease, basis of the relative's diagnosis, among other things.

Within this clinical history, prior lab and radiology information pertinent to the diagnosis is captured. The clinical history is summarized in the form of diagnosis: the working diagnosis and differential diagnosis, as well as co-morbid disease processes, among other things.

The history of the present illness documents the data supporting the preoperative working diagnosis. The supporting symptoms and signs, as well as pathologic diagnoses can be captured by, among other ways, the ICDS 9 codes.

Under each diagnosis found in clinical history, a hierarchical series of ICDS 9 codes are arranged from the broadest and most inclusive diagnosis followed by the ICDS9 codes for the supporting symptoms. The ICSD9 conventions specify pathology and location as well as grading as to the severity. For example, most disease processes are set up in 1, 2, 3 manner (mild, moderate or severe). Additional special disease processes are defined by lab values, such as heart disease, 30 percent occlusion of vessels, versus 60 percent, versus 90 percent. The ICDS 9 codes typically accommodate all of this data, with expanded and high resolution (specific) coding of the patient's condition being the insurance and hospital industry standard. The lesser codes catalogue symptoms, physical exam findings, and impressions such as: "right lower quadrant pain", "angina pain", "tenderness", "immobility of knee". The second tier of codes would also annotate location and severity. The catalog of symptoms and clinical signs find ready application during surgery, as the surgeon assesses the physical findings upon opening or laparoscopy and tries to correlate the intra-operative, pathological findings to the patient's actual complaints.

Past medical history (PMH) includes the diagnoses, both active and inactive, that are established in the patient's medical history. PMH diagnosis are set up in a hierarchical priority as to impact on life, and graded as to how assured the diagnosis was established.

The past medial history module documents methods confirming the diagnosis: whether based on clinical signs and symptoms alone, versus radiographic proof, versus surgical and biopsy proof The PMH may include diagnoses made by various physicians. Oftentimes, the surgeon and anesthesiologist need access to the diagnosing physicians; therefore, each diagnosis needs to include a data link (telephone number, email) to the physician who made the diagnosis, and the physician or entity that is currently managing that problem. If the problem diagnosis rises to significance, the managing physician could be readily consulted to aid in evaluation and management.

A full catalogue of the patient's drug and environmental allergies is included, comprising the allergen substance and the resultant adverse reaction. The adverse reaction would be specific: anaphylactoid reactions versus hives, versus dyspnea, versus psychological dread. Additional piece of information with each substance or allergen would be the certainty that the reported allergy is true.

The catalogue of the patient's usual medications includes pharmacologic substances (prescription, OTC, and herbal/folk medicines) that are taken on a regular basis. The list includes the name of the medication, dosage, administration directions, and prescribing physician. Data would include when the medication was started, the degree of patient compliance, and the time and date of the last dose.

The past medial history module includes the family disease history, and specifies the disease and afflicted individuals in the family tree, as well as the method of confirmation (hearsay versus autopsy, laparoscopy, surgical or conjecture). Additionally, family history could include information, such as, but not limited to, on anesthesia reactions and malignant hyperthermia.

Laboratory findings references preoperative data not including the stream of current lab values generated within the surgery. These baselines include the various tests (CSC, Dig Level, chem. screen, etc.), with times, dates, and if applicable, a trend graph of the multiple data points for lab drawn on a repetitive basis. Catalogues provide precise alphanumeric tags of laboratory tests and values.

Radiology studies include the type of study, date, facility, and radiologist. It will have a summary of the findings typically found in radiographic reports. If the radiograph image is a portion of an electronic data pool, the retrieval address and code would be included to summon the image for OR viewing. This includes EKG, echocardiography, and pulmonary function test results reported in the standardized language of the American College of Cardiology and Pulmonary Medicine.

Notable physical findings that the surgeon and anesthesiologist want referenced would be compiled into a database log according to the routine history and physical (H&P) format. These significant findings include: measurements, locations, and data that should be correlated with the patient's complaints in the history of present illness (HPI), and the intra-operative findings at the time of exploration. The physical findings data aids in confirming the surgical site (left, right, anterior, posterior) and determines the incision site.

Anesthesia would also focus on the airway to include Mallenpetti Class, Grade on previous direct laryngoscopy, dental status, and range of motion during neck extension, among other things.

The present patient physiological state is established. The current patient data includes, among other things:

Location—The LED or RFID tracking system will note the patient's exact location in the room at any given time;

Position—In what physical position on the operating table is the patient, such as, but not limited to, Trendelenburg tilt or specific surgical position such as dorsal lithotomy, along with the time durations in each position;

Tourniquet Time—Tracks the duration that specific vessels are clamped closed, with alarms based on current recommendations;

Pump and Shunt Times—Tracks the duration that specific bypass type devices are employed;

Cardiovascular Vitals (CV) Signs—Includes pulse rate, blood pressure, oximetry data and cardiac tracing. EKG type descriptors such as regularity versus irregular rhythm and segment changes would be recorded. Many existing software packages employ automatic cardiac tracing analysis programs that are able to recognize rhythm and segment changes. Access to prior EKG tracings via the past medical history (PMH) allows comparisons to be made intra-operatively. When other more invasive instrumentation becomes necessary, the CV signs could be expanded to record, such as, but not limited to, blood gas readings, and arterial pressures. The entirety of the CV signs data is captured electronically from the patient monitoring and anesthesia systems; and Pulmonary Data—Includes tidal volume, inhalation and exhalation volumes and pressures, O2 saturation, and end tidal CO2 saturation derived from anesthesia machine system.

The state of the OR system is established, in accordance with an embodiment of the present invention. Referring again to FIGS. 2 and 3, the OR characteristics that are stored in the system agents include the dimensions, contents, temperature, pressure and airflow, among other things. It also includes safety items such as smoke and fire detectors, electrical load, among others. The information of each of the OR entities create a virtual blueprint and detailed equipment map. The room attributes would include the scheduling requirements for the intended surgery which is linked with the hospital's information and logistic system.

The surgical table is characterized. Table position and configuration define the current function. The configuration includes the attachments and the way the table is physically folded to support the patient in precise surgical position for anatomic access. The configuration might be in a lithotomic, supine, colorectal or neurosurgical configuration. Configuration also includes table tilt (inclination, declination, or lateral tilt). These variations impact the patient in terms of stress on patient joints, difficulty with breathing or ventilation, among others, making the location of the table within in the OR floor plan and its relationship to the actors and furniture a pertinent concern.

Identification and tracking of instruments and expendables, among other things, is provided, in accordance with an embodiment of the present invention. To facilitate identification and tracking, a tracking device, such as, but not limited to, radio frequency identification (RFID), is utilized. The item has associated with it a RFID tag that can be sensed by sensors within a given RFID sensing field.

Figure 11:
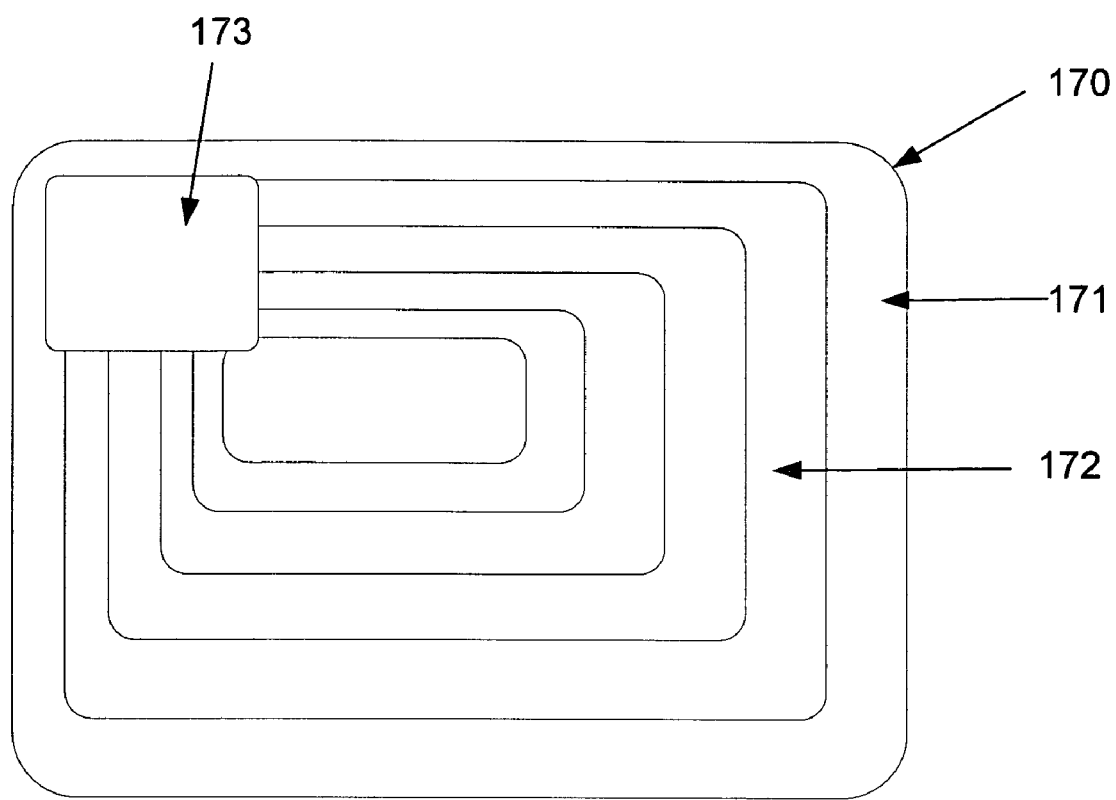
FIG. 11 is a top view of a RFID sensor sheet, in accordance with an embodiment of the present invention.

FIG. 11 is a top view of a RFID sensor sheet 170, in accordance with an embodiment of the present invention. The RFID sensor sheet 170 comprises an antenna array 172 coupled to a film 171, and electronics 173. The electronics 173 provides power and a communication means for coupling to RFID detection electronics and wired and/or wireless communication electronics to communicate sensor data to an access point connected to a computer platform that supports the system's RFID middleware. The wireless communication transceiver provides a no-touch conduit to adjust the RFID's performance settings. The unit includes a self contained rechargeable battery power source.

Figure 12:
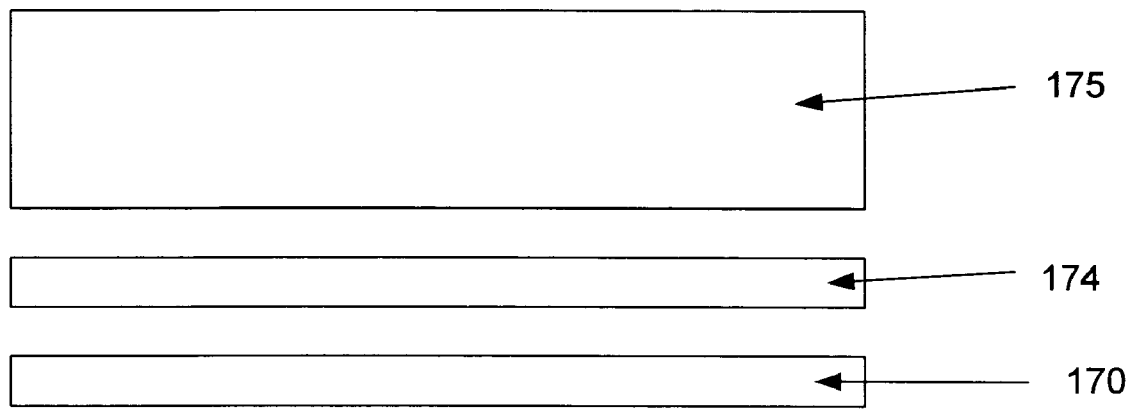
FIG. 12 is a side view of the RFID sensor sheet, in accordance with an embodiment of the present invention.

FIG. 12 is a side view of the RFID sensor sheet 170, in accordance with an embodiment of the present invention. The antenna array 172 is adapted to create a specific volume of space 175 that an RFID tagged object will be reliably detected. The film 171 serves as a platform to mount the antenna array 172 to any suitable surface 174, such as, but not limited to, a table top.

The RFID sensor sheet 170 provides for rapidly configuring any work surface or work space into an RFID sensor shell for tracking RFID tagged objects within the work environment. The RFID sensor sheet 170 readily turns a chosen surface, such as a countertop, into a waypoint sensing station to monitor both inventory (material flow) and process flow. Sensor shell waypoints are logically chosen from key locations derived from the process model and in turn, the information captured from these waypoints of the sensor shell provide a source of metrics to manage the overall process.

Figure 13:
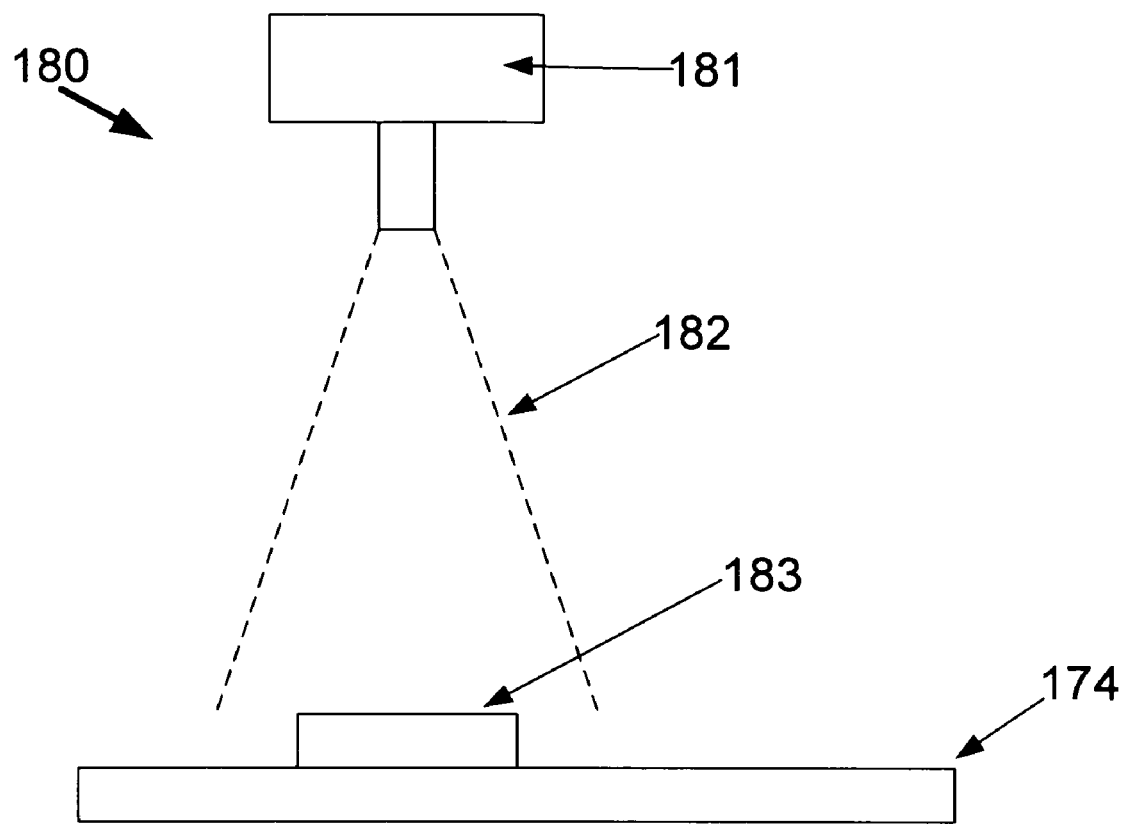
FIG. 13 is a side view of a video tracking system, in accordance with an embodiment of the present invention.

FIG. 13 is a side view of a video tracking system 180, in accordance with an embodiment of the present invention. The camera 181 is located such that its field of view 182 is able to image a work object 183 that is placed on a work surface 174. The sensor shell accommodates video images from a wireless video camera 181 mounted above or in similar manner so that the camera 181 has an unobstructed view of area of interest. The camera utilizes adhesive or conventional mounting methods. The camera includes identification means, including, but not limited to, barcode readers and microbar code readers.

In accordance with another embodiment of the present invention, the RFID sheet 170 of FIG. 12 and the video tracking system 180 of FIG. 13 is used in combination.

The RFID sheet 170 antenna array 172 provides a discreet sensing volume. In effect, the system creates an "RFID box" that registers the identity of the RFID tagged item place within. The video image and barcode information provide primary data or redundant data. The film 171 is provided with adhesive such that the RFID sheet 170 can readily be placed and adhered onto or under a shelf or cabinet. Once the RFID sheet 170 is in place, the RFID box or volume 175 is on the shelf, ready to act as a sensor for that particular work or storage station. The RFID sheet 170 is readily mounted onto cabinet shelves, table tops, doorways, segments of conveyor belts, in corners of the room, on walls, on ceilings, among others. The adhesive provides for rapid installation of the RFID sheet 170 creating useful reception volumes and shapes. In an embodiment, the film 171 serves as a platform to mount the RFID electronics and a wireless transceiver 173. Mounting the components together as a single package makes the physical installation of the "RFID box" a simple single step. A RFID sensing shell is readily created in the given room or in multiple rooms by utilization of wireless technology.

In accordance with another embodiment, the RFID electronics 173 comprises a control means to adjust the gain of the antenna array 172 to adjust the volume 175 above the surface that one wants to capture information. This in turn determines the sensitivity and the performance in terms of false positives and negatives of the system. The sensitivity of the antenna array 172 and other items is controlled through the wireless transmitter of the electronics 173.

The economic importance of this hardware implementation is that a tracking system for virtual simulation and a virtual world is created. The hardware implementation is adapted for retrofitting what already exists without incurring great installation expenses.

In other embodiments in accordance with the present invention, the RFID sheet 170 is coupled to the work surface using any suitable means, such as, but not limited to, mechanical fasteners.

Figure 14:
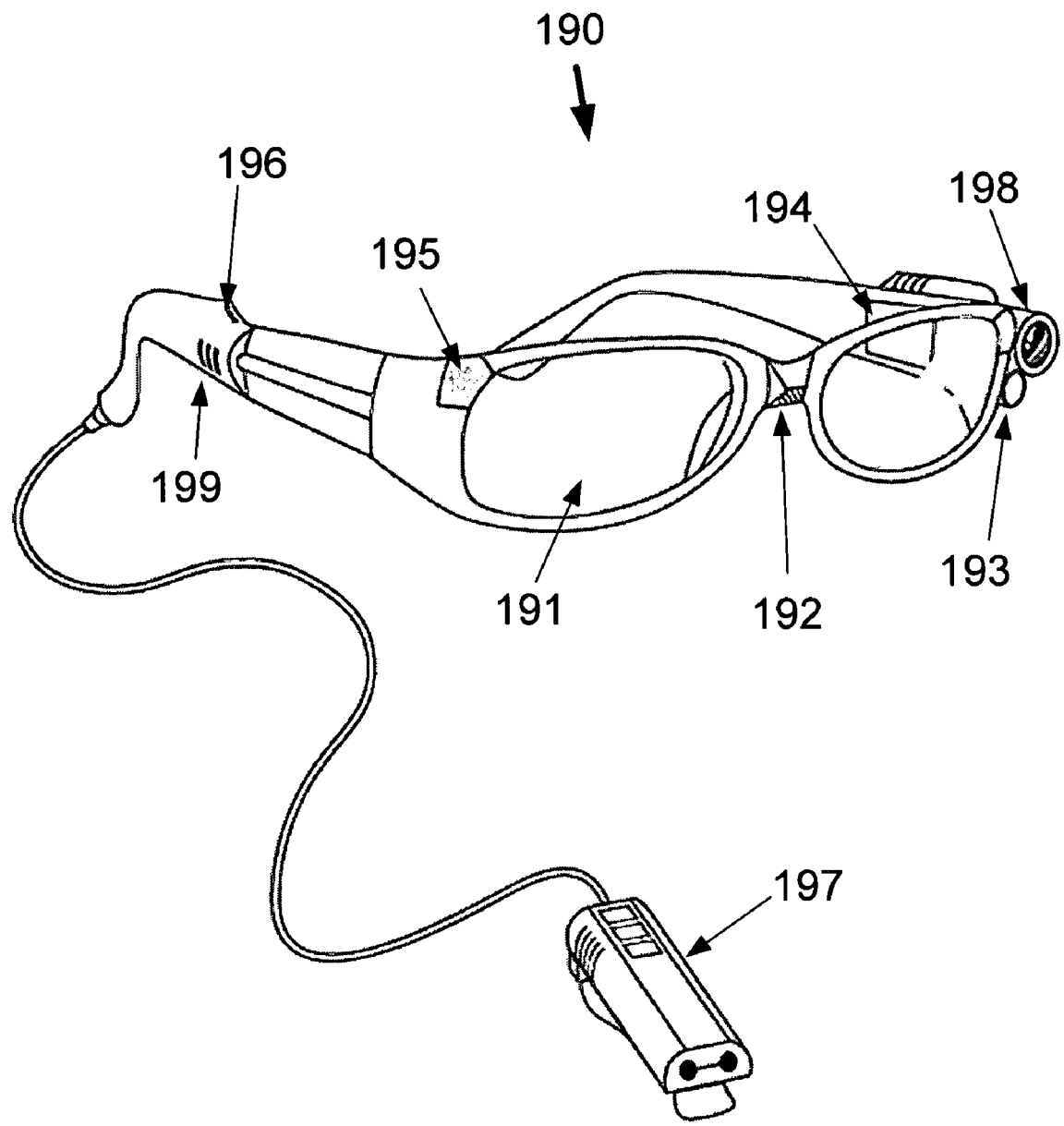
FIG. 14 is a perspective view of a headset, in accordance with an embodiment of the present invention.

FIG. 14 is a perspective view of a headset 190, in accordance with an embodiment of the present invention. The headset 190 comprises eyeglasses 191, a camera 198, a light 193, a microphone 192, an LED display 195, and antenna 196, headphone electronics 199, and transmitting electronics 197. A light weight microphone 192 and headphones 199 are integrated into the protective glasses 191 providing a convenient intercom headset network that remedies many of the acoustic problems within the OR. The controller 197 is adapted such that a user can direct a command toward a particular individual, wherein the volume is increased sufficiently for the target individual to take notice and the command to be heard. In the other individual's headsets that are not the target of receiving the message, the message would be quieter. An example includes a surgeon asking for a mayo scissors would be as such: "pass mayo scissors" and this would be preferentially amplified in the headset of the scrub nurse, who would physically pass the scissors. An example of the selected volume enhancement would be a surgeon request for a specific stapler that was not on the sterile field. The inventory control manager would know where the various items were and since it would not be within the sterile field, the circulator would also receive the request. Therefore, a request such as "pass or obtain endo GI stapler V12" would amplify in both the circulator and scrub tech's headset but would be muted to anesthesia. Certain key words like "attention" could be interpreted by the controller to ensure the message is passed to all within the room at a suitable volume for understanding. The communication system described above could function in the above "smart mode" or an "open channel" dependent on the team's desires.

Referring again to FIG. 3, the surgical situation display 20 (SSD) serves as a visual reminder of the central goal and sub-goals to achieve the desired endpoint. The requirements for successful goal accomplishment fragments into a multitude of decision tasks, physical execution to the surgical procedure, maintenance of anesthesia and patient wellbeing, and all the logistical support tasks to make the surgery possible.

There are also forms of passive communication in that the surgical image and agenda board provides a reference to the circulator, other technicians and anesthesia as to exactly what portion of the procedure is being conducted at the immediate point in time. In addition to surgical images, agenda and record information such as medication logs and fluid balance logs are passive forms of communication, which help to orient the team members and cut down on extraneous questions.

Actor Characterization

Surgeon identification is established by means such as, but not limited to, hand written signature, voice recognition, fingerprint and iris signature. Once positively identified, the surgeon is marked with a tracker beacon fitted onto their protective glasses, which emits their specific RFID/LED transponder code. The transponder tracking system monitors the surgeon's location, position and posture, and field of view. The tracking data set helps objectively define the surgeon's present state on a moment-by-moment basis.

The protective glasses are provided with eye movement sensors to determine the object the surgeon is looking at.

Current activity is tracked to characterize what is the surgeon is currently involved with, such as making the opening incision, analyzing findings, planning an action, resting, and taking an urgent phone call, among others.

Human stress and strain is tracked and characterized. Human factors data includes fatigue, social stress, strain, among others. Reaction time and cognitive reaction time is monitored.

Surgeon's Preference Card is characterized. One of the most indispensable pieces of information for the surgeon is instrument and equipment preference to accomplish particular procedures. Smart system 100 defines this for planned procedures, as well as at what occurred ad hoc within the progress of the surgery. A surgeon's preference card would include such things as: ergometric aids including stools, corrective glasses, surgical glove size and type, steps; logistic requirements (chromic versus Vicryl, versus permanent sutures); type of needles; type of staples; sequence; and standby equipment, among others.

The state of the surgeon includes capabilities defined by qualifications, training and experience. The credentials include board status, specific training, hospital credentials, total volume of the specific type of procedure, and possibly the date of last similar case.

Anesthesiologist data would be similar to a surgeon's: identify, qualification, preferences and equipment needs, which are dictated by the type of case being performed, and the patient's body habitus and medical history. What the anesthesiologist is currently doing is an important piece of information. In addition, CRNA Anesthetists require back up MD/DO anesiologist backup in case an anesthetic event occurs outside their scope of practice or individual capabilities and documentation of anesthesiology and their location.

The first assistant is identified, RFID/LED marked and confirmed, along with the other qualifications. The first assistant preferences would include ergometric aids such as stools, corrective glasses, surgical glove size and type, steps, among others. Activities of the first assistant are tracked.

The scrub nurse is identified, RFID/LED marked and confirmed, along with the other qualifications. Scrub nurse preferences include glove size, lifts, and various ergonomic aides required to perform a job. What the Scrub nurse is currently doing is tracked.

The circulator is also identified, RFID/LED marked and confirmed, along with the other qualifications. The circulator performs the majority of documentation and supply retrieval tasks; therefore, her or his specific display and interface monitor configurations would be included in the preferences. Activities of the circulator are tracked.

Other technicians and OR personnel have substantially similar considerations and tracking.

Equipment Characterization

The anesthesia machine is characterized. State data includes the contents within the reservoirs of anesthetic gas, the tubing to deliver the anesthetic, and the monitors and associated devices for the delivery and elimination of the anesthetic, including vacuum pressure for suction, pipeline gases O2, N20 and air, and circuit size pediatric vs. adult. The manufacturer's model number, serial number, modifications and maintenance history form the central points in identification. The operating status, error codes, self test data and internal operating data contained in the internal electronics provide a source for defining the current operational status of the machine. Gross functionality is confirmed with the daily and pre-case checks by the supervisor and operator. Also included is important anesthesia machine data on "state", including location of backup units and parts within the hospital.

The patient physiologic monitors are characterized. These electronic sensors define patient physiology such as EKG machines, pulse oximetry, arterial blood gas, among others. Each component has an operational state whether it is working and providing patient data. Internal operational data includes device settings, self-test status, error codes, and internal function data that the devices may share. Switchology is often the problem when things fail to work; therefore, the switch configuration is included in state data. Also included is the location of spare expendable attachments, such as leads and catheters.

The Intravenous System is characterized. The administration system includes: type, rate and volumes of fluid being administered noting flow, total amount administered, and the amount still in reserve in the bag; location of the IV port(s) (commonly, there are multiple IV sites running at one time, so the "state" data of each fluid type and IV site is continuously monitored; central line administration of fluids; status whether the overall system is functioning as defined IV fluid and drug plan; port information, including who placed the IV site and when; hardware considerations, including types of IV pumps, serviceability, capabilities and the electronic communication protocols available to extract that data; patentancy and gauge or lumen size, including different lumen sizes are required for different uses of IV administration such as blood product, crystalloid resuscitation versus total peripheral nutrition, among others, and information regarding the component spares and their locations.

The endoscopy system is characterized. The endoscopy systems provide a visual reference for evaluation of the surgical site, facilitates instrument movement within the operative workspace, and enables assistants to aid accomplishing the procedure itself. Endoscopy may have photo integration methods as well as video image enhancement. Endoscopy and laparoscopy systems are typically of three components: the optical component, the camera, and the lighting.

Specific information is cataloged within each subsystem:

Endoscope/laparoscope Optics (Optical component)—An endoscope is characterized by usual use, such as colonscope, laparoscope, cystoscope, and hysteroscope, rigid or flexible, shaft diameter, length and lens angle. Within the identifying data are the manufacture, model and serial numbers. The identifying and characterizing data determine compatibility with different light cords, light sources and cameras. Service records provide necessary information, including the validation of broken optical fiber test and if there is any history of scratches or fluid leakage into the optical elements. Another type of optical information is the presence of anti-fog lens coating. Additional information on capabilities including presence of an operating channel, laser compatibility, and photo interrogation capabilities is provided. Location of spare scopes and adaptors is characterized in event of equipment failure or component incompatibility.

The video camera is characterized. Camera data includes the type of camera: manufacture, chip, coupler size and compatibility, resolution, error codes, performance data, maintenance and manufactures notices. Switchology is often the problem when things fail to work therefore the camera control box switch configuration is included in state data.

The endoscopic light source is characterized. The identity and characteristics of the light source is defined as to if it is operable, compatible with endoscope equipment, amount of illumination currently being produced, the type of mode, including automatic illumination, auto shutter versus manual, and error data from the internal workings. Other data within the maintenance history might include the last time the light was changed, the type of light it needs, is there a spare light in the house if it goes down and where it is located. Switchology is often the problem when the endoscope system fails to work therefore the light source control box switch configuration is included in state data.

The fiberoptic light cord is characterized. The identity and characteristics of the light cord includes manufacture, model, inventory number, cord diameter, length, coupler type and compatibly. Operability data includes the current light transmissibility percent of the cord and maintenance history.

The patient image monitors are characterized. In an endoscopic procedure, commonly there are monitors, such as a cathode ray type television screen to display the patient image. These monitors have basic technical specification and capability, which would be part of the state. In addition, the state includes the source of signal it is currently displaying, if the monitor cable connections are secure and carrying signals normally. Switchology is often the problem when the endoscopy system fail to work therefore the monitor switch configuration is included in state data. Any error codes and problems noted within the monitor are also characterized.

Beyond operation there is the monitor's physical location and position in relationship to OR floor plan, the actors and other "furniture." Ergonomic considerations include the height for comfortable viewing by the surgeon, assistant and the rest of the surgical team as well as correct screen tilt necessary for glare reduction.

The electro surgical system is characterized. Electrical Surgical Units (ESU) cut, coagulate or destroy tissue via electrical current heating effects generated by microwave-type interactions upon the tissue at the instrument tip. Commonly, monopolar ESU generators produce specific wave trains sculpted for cutting functions or for coagulatory tissue effects. The wavetrains deliver high RMS wattages to the tip of the bovie pencil and hence the patient. The monopolar ESU instruments require a secure patient grounding pad to prevent electrical burns distant from the surgical site due to a grounding fault. The monopolar ESU contains self monitoring circuits that alert the OR staff via error codes and associated hazard data. The specific operations data available to be shared depends upon the machine's processing electronics and availability of communication ports. The location of the ESU box and bovie tip is characterized. The different cord compatibilities and location of spare accessories is characterized.

A second type of ESU is a bipolar current generator which directs the EMF energy between two closely spaced "Kleppenger" paddles: the first paddle for current delivery and the second paddle scavenges the electrical energy so to minimize collateral burn or damage. The Kleppenger paddles provide a means to localize application of coagulation energy. This instrument, in addition to wattage, has current flow measurement. The current flow measurement determines if something is thoroughly desiccated and hence adequately coagulated by the bipolar devices. A variant of the bipolar devices is the bipolar scissors, in which the paddles are incorporated into scissor blades for electro-coagulation prior to cutting the captured tissue.

Another variant of electrical instruments is the argon gas coagulator that delivers current through a gas stream of argon directing the ESU energy to the desired point of treatment.

Lasers are identified as to manufacture, model, serial number. The attributes would be the type of laser, the calibration of the laser and its operating specification. The settings include the type of wave train, including pulse, super pulse, continuous, and power density delivered. Other information includes compatibility of the laser to other equipment such as laparoscopy, hand ports, and operating microscope. Operability data includes internal diagnostics and self test codes, maintenance history and pre-case inspection status.

As new personnel or equipment is introduced to the OR, a model would be composed to define his/her/its state and function.

In terms of pertinent data though, only certain pieces of this data would be pertinent and only at certain times. The systems agent will apply methods as to what and when to communicate.

Instruments are characterized. Instruments provide for physical manipulation of tissue and can be grouped according to physical operation such as clamps, staplers, finger forceps, scalpels, among others. Surgical instruments include all of the nondisposable instruments within the OR as well as one-time use disposable instruments such as laparoscopic Metzenbaum scissors. The instrument state is defined by the standard nomenclature based on catalog code, dimensions and material characteristics. Each instrument possesses a specific name, catalogue number, as well as the inventory identification number. To facilitate machine vision and scanner identification, micro barcodes could be etched in multiple places on the instrument as to identify it. Within each instrument's database is the maintenance history, including whether the instrument is sharp or dull, whether it works correctly, whether it has problems that make it unserviceable, when was it last sterilized, is it sterile or nonsterile, has it exceeded shelf-life for sterility, among others, and the location of spare instruments.

Materials and supplies, such as sponges are characterized. Each individual entity would be identified along with its attributes: manufacture, radio or non-radio-opaque; RFID marker and code; IR marker and code; dimensions; current location; prior location, including the supply room, on the back table, on the mayo stand, and within the wound and patient's body cavity; sterile or contaminated or soiled; what is the item's final disposition, is it in the trash can, has it been transported away from the OR, and the location of spare sponges, among others.

Clips come in various sizes and various materials, such as stainless steel, titanium, dissolvable plastic. They are catalogued as to what their purposes are. Most clips are housed in disposable clip appliers; however, some clips use permanent instrument clip appliers. Like other instruments and objects within the OR, the clip application system has location and serviceability requirements. The disposable clip appliers are identifiable, such as with a bar-coded similar to the other nondisposable instruments and be named according to catalog code and standard nomenclature. Means of ID tracking is provided. Location of spare clips is included in the database.

A suture is a strand of sterile cord that can be plain or attached to needles. A suture's characteristics include: needle type and size, suture material, including Vicryl, silk, and prolene, length of suture material, and caliber. Sutures have, as with some of the other materials, status as to whether used or unused. There are free sutures without needles referred to as free ties that are packaged in groups of five identical pre-cut strands. The free tie suture strands pose no significant hazard in themselves even the non-absorbable materials rarely cause mischief. In terms of automatically identifying the sutures by sensors, both needle and plain sutures are typically packaged in foil pack containing a plastic holder. Barcode is placed on either the plastic holder or foil package. Until the suture item is called to use, most scrub techs do not remove them from the package or disposable plastic needle guard holder. Therefore, the package provides a marker as to the location of suture and needle. In terms of free sutures, similar bar-coding could tell you how many were used and opened.

Airways are an integral part of anesthesia delivery. There are different types such as intratracheal tubes, LMA versus varied types, among others. They come in lengths and caliber. They all have state, including location and availability. Knowing the patient's weight, height and age allows the call-up suggesting suitable airway size.

Tubes include other tubes such as Foley catheters for urinary drainage; possible wound drainage devices such as Jackson Pratt drains, joint drainage type devices such as Penrose. All of these have type and substance, length and caliber. They are amenable to bar-coding. They also have the need for marking as to location and status of use, unused or discarded.

The surgery is a process that physically alters the patient's anatomy through incision, drainage, excision, reconstruction, implantation, among others, in order to diagnosis and treat. The surgical process transforms the patient's physiological state to a more advantageous state for healing, function, cosmesis and the relief of suffering.

The team members must anticipate the next steps in the central and parallel process. Smart system 100 prompts will cue the OR team members what the functional model anticipates as well as a prompt for free thought.

Beyond basic standards and safety limitations, there is likely a best practice for any given procedure, patient, surgeon, and facility. Moreover, within classes of procedures and patients there are likely to be best practices within the procedure itself. The resultant guidelines of "best practice" for applying a specific operation may include indications, contraindications, operative time limitations, the type of suture used, the type of stitch or the sequence of procedures, among others. By the analysis of the work of expert surgeons in similar situations, one can get clues as to what that best practice is and more importantly, what are the key decision points of best practice, including doing something a certain way at a certain time for the best possible outcome. Best practices include the steps of particular procedure, including what is necessary and unnecessary. Presently, many of these fundamental surgical issues cannot be answered despite vigorous debates about surgical practices occurring in the various surgical communities and subspecialties.

Smart system 100 provides a master framework for organizing and testing the multiple hypotheses of the "what and how" mechanics being debated. With an appropriate analytical framework the decision points, technique, and patient parameters will come into focus. Smart system 100 will gather sufficient data by providing a large enough surveillance network to gain the statistical power necessary to determine what best practice is. Once the methods of best practice are recognized and the guidelines defined, smart system 100 will be a conduit to disseminate that knowledge to the surgical team in the OR.

In terms of direct support of the surgical process, occasionally there are unexpected findings that surface, including what to do with an anomalous vessel, what to check for, among others. Many times, there may not be another expert surgeon to provide advice for the surgeon confronted with the unexpected to make optimal decisions. First, by providing software input as to critical features of a given contingency or in effect an intra-operative emergency checklist will clarify the surgeon's thought. Additionally, through video link, and/or auditory link, an expert surgeon can be found real time to offer advice.

Looking at the logistical support of surgery, many times the circulator, scrub or supply clerk is lost in details and cannot focus on the task at hand. Smart system 100 provides the available reference within the OR for information about the equipment and instrument management tasks required of them to accomplish their assigned tasks efficiently. Certain equipment, such as some staplers, has an intricate setup. Many times the individual has had limited contact with the device in question and he/she may require a brief focused tutorial. Successful surgery requires the OR team to possess and nimbly apply a great deal of knowledge about the surgical operation, its logistical support, and various contingencies plan for common complications. The required information is made readily available in conveniently usable form for all team members within the OR.

Smart system 100 continually reminds the actors of their goals, their weaknesses, and provides a personal notebook or virtual coach at ready reference to prompt the actors on what to do in a procedure. Coaching and visualization has been shown to enhance performance. Expert surgeons have images and rehearse the procedure mentally prior to stepping into the operating room. The coaching notebook presents relevant data, clues, as well as other human performance enhancement tools for relaxation and visualization.

Smart system 100 provides the management of the full spectrum of the OR's permanent surgical equipment, instruments, expendable supplies, medications and disposable devices. Smart system 100 accommodates identifiers, such as, but not limited to, barcode, RF/magnetic markers, and transponder systems to track these items. System 100 tracks all supplies, down to every last sponge, needle and clip. Equipment information, including temperature, electrical resistance, and actuation time, is gathered for determination of pre-failure patterns that indicate impending failure.

Conventional surgical instruments include scalpels, clamps, and endoscopic instruments, among others, are characterized and tracked. The flow of instruments to and from the surgeon is tracked, the ready availability of the instruments is determined, the state of the instruments present is determined, and the recording of the specific instruments used is recorded for billing.

Disposable devices include staplers and suturing devices, are characterized and tracked. The flow of devices to and from the surgeon is tracked, the ready availability of the devices is determined, and the recording of the devices used is recorded for billing, and the recording of the devices used for disposables inventory management.

Expendable materials management, including sutures and clips is characterized and reported. The flow of materials to and from the surgeon is characterized and tracked, the ready availability of the materials is tracked, the recording of the materials used for billing, and the recording of the materials used for "disposables" inventory management.

Sponges and lap pads are characterized and tracked, including complete tracking of sponges and lap pads placed within and in transient to the surgical site, the ready availability of the sponges and lap pads, the recording of the sponges and lap pads used for billing, and the recording of the sponges and lap pads used for "disposables" inventory management.

Medications are characterized and tracked, including the timely flow and availability, ensuring that the correct medication is administered to the patient, ensuring no obvious medical contraindications or allergies before administering medication, ensure the correct route of administration, including oral, IV, 1 M, other modes, ensure the correct dose of medication is administered given the body weight, BMI, surface area, renal or liver function of the patient, and documentation of the above.

IV fluids are characterized and tracked, including timely availability, ensuring the correct flow rate, ensuring correct IV fluid type is selected for electrolytes and patient condition, recording total fluids, and verifying correct medications and dose of medication in IV fluid.

Pump fluids are characterized and tracked, including timely availability, correct type check, ensuring no evidence of overload of fluid balance, and correct pressures.

Implants, including vascular, orthopedic, and others, are characterized and tracked, to ensure that the intended implant and alternates are in house prior to patient entering OR. The flow of implants to and from the surgeon, the ready availability of the implants when needed, the recording of the implants used for billing, and the recording of the implants used for "disposables" inventory management is provided.

Critical spares, including equipment and supplies is characterized and tracked, including emergency medications for anesthesia and code conditions, extra sutures, clips, and expendables for emergencies such as bleeding, and key disposable instruments that tend to break or malfunction such as bipolar cautery.

The anesthesia machine is characterized and tracked, including the service record to ensure gases and anesthetics medications are of the correct type and sufficient reserve, certified operable, and that the standard operations check is done.

Anesthesia ancillary equipment, such as the laryngoscope, is characterized and tracked, including the service record, certified operable, and the standard operations check is done.

The OR table is characterized and tracked, including the sanitary condition, whether configured, operable, and whether the correct attachments are available and functional.

Patient monitors, including automatic blood pressure cuff and EKG, are characterized and tracked, including the service record, whether certified operable, and the standard operations check is done.

Electrosurgical units are characterized and tracked, including the service record, whether certified operable, the standard operations check is done, ancillary expendable equipment is compatible with the machine, including the cord types and plug types, and all connections are firmly secure, including patient ground pad.

Endoscopy equipment is characterized and tracked, including the service record, an operable light source serviced and operable insufflations, serviced and operable camera and monitor, and serviced and operable photographic equipment.

Maintaining correct equipment position during surgery is characterized and tracked, ensuring that the cords and connections can reach, ensuring that monitors are visible to the team members without obstruction, ensuring the lights are adjusted and positioned for optimal illumination of the surgery and support activity, ensuring the patient position is adjusted according to the needs of the surgery, such as the Trandelenberg position, high lithotomy/low lithotomy, tilting, among others, power settings and operating parameters adjusted properly, ensuring furniture such as mayo and back table or ergonomically placed, and ensuring proper surgeon and assistant ergonomics such as step stool, among others.

The business message traffic is prioritized. There are some messages that have a higher priority than other messages. The dispatch of outgoing calls and messages is important. At times, there are moments that the surgeon or other members can talk to someone else by telephone. At other junctures, email messages or voicemail messages may be more appropriate. In terms of email and voicemail messages, there are some standard problems, such as to increase the dose or decrease the dose, which a menu of the standard problems or questions is provided and an alpha numeric message dispensed via hospital network or internet.

Verbal messages of medication changes is printed on one of the situation monitors so that the physician, nurse, or anesthesiologist who is handling the call will actually see what they are sending and verify prior to sending the message. In terms of some hospital business, more reliance on written messages makes better assurance of proper action on the part of the recipient.

The Internet is a very useful modality in terms of accessing information and expert help. Internet can be used for sending patient images, verbal transmission as well as eye-to-eye contact with expert help. The expert could receive the surgical images, obtain the medication log, vital signs, among other things. Access to a broad array of data and images enables the expert tele-consultant to readily understand the situation and give sound advice via the Internet.

There is advice and information within the hospital that many times is not readily available. Prior radiographic studies, lab tests, or discussions with the radiologist or pathologist may be needed intra-operatively. Using smart system 100 in communication with the hospital network, one can access these images and access direct discussion with the experts. Similar activities can be done with logistical support and actually talking with the supply clerk and having them display an item to the circulator prior to sending it up.

Within the hospital network connection there is also medical records that may be more extensive and have free stream data not available on the patient's state module or the patient agent software. This could be accessed if need be or dispatched if in paper format.

Hospital network connections are also helpful for querying in-house physicians that are logged in. For example, a surgeon in the OR can communicate with an urologist if needed for a particular opinion or for surgical assistance. The system can query the hospital database and if there is an individual with the qualifications available, that person can be paged and immediately brought to the OR to render assistance or advice. This prevents searching for a particular doctor. Also this method is used to make telephonic connection or audiovisual connection with specialty people that are on the hospital network that may or may not be in-house.

The sensor shell and system/function agent-based software combination that is based on the desired process model may have application in manufacturing and other domains. Tracking sensors in accordance with embodiments of the present invention allow for the rapid and relatively inexpensive installation of a RFID/video/LED sensor shell into rooms and on specific furniture.

In other embodiment in accordance with the present invention, smart system 100 is operated at planes of automation and intelligence suitable for a particular purpose. Smart system 100 can be configured from a basic reminder and documentation aid to evolve into an "expert system" to implement TQM and safety countermeasures and finally a system that can learn and make suggestions to enhance the surgical/healthcare/work environment.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

The invention claimed is:

1. An intelligent human-machine interface comprising:
   an interface shell;
   one or more system agents including one or more dynamic, knowledge-based software object sub-agents that model and track the state of a work area thereby creating a virtual blueprint of objects contained in the work area; and
   one or more function agents that model, track, and facilitate work area functions, the interface shell that provides a hardware and software interface between the one or more system agents and the one or more function agents;
   a dynamic documentation system in communication with the one or more function agents and one or more system agents;
   including a layering architecture, comprising:
   a tracking layer;
   an equipment and supply management layer that takes the information from the tracking layer and processes the information in regards to records, inventory and maintenance systems;
   a coordination layer that takes information from the tracking layer and the equipment and supply management layer to develop an image of what is occurring in comparison to what an overall plan is based;
   a situational awareness layer in communication with the tracking layer, the situational awareness layer that provides output features of relevant information to the various interfaces; and
   an oversight layer that combines the information from the situational awareness layer with process rule sets contained in the one or more function agents to determine if processes are being performed correctly, wherein the layering architecture is created by threads of tagged data relevant to a particular function, wherein the interface shell, the one or more system agents, the one or more function agents, the dynamic documentation system, and the layering architecture that process an integrated collection of facts and relationships and to recognize deviation from or compliance with a predetermined process and communicate deviation from or compliance with a predetermined process to a user.

2. A method for providing an intelligent human-machine interface comprising:
   providing an interface shell;
   providing a one or more system agents including one or more dynamic, knowledge-based software object sub-agents that model and track the state of a work area;
   providing one or more function agents that model, track and facilitate work area functions, the interface shell that provides a hardware and software interface between the one or more system agents and the one or more function agents;
   providing a dynamic documentation system in communication with the one or more function agents and one or more system agents;
   creating a system hierarchy model of the structural elements of a system model and a functional model;
   identifying a set of sensor, actuator, and communication systems necessary to implement functionality;
   identifying component and interface specifications for the acquisition and integration of the physical components;
   creating functional model software specifications; and
   utilizing a model based knowledge base to construct the hierarchy and operations, wherein the interface shell, the one or more system agents, the one or more function agents, the dynamic documentation system, and the layering architecture that process an integrated collection of facts and relationships and to recognize deviation from or compliance with a predetermined process and communicating deviation from or compliance with a predetermined process to a user.

3. A method for providing an intelligent human-machine interface comprising:
   providing an interface shell;
   providing one or more system agents including one or more dynamic, knowledge-based software object sub-agents that model and track the state of a work area; and
   providing one or more function agents that model, track and facilitate work area functions, the interface shell that provides a hardware and software interface between the one or more system agents and the one or more function agents;
   providing a layering architecture, comprising:
   a tracking layer;
   an equipment and supply management layer that takes the information from the tracking layer and processes the information in regards to records, inventory and maintenance systems;
   a coordination layer that takes information from the tracking layer and the equipment and supply management layer to develop an image of what is occurring in comparison to what an overall plan is based;
   a situational awareness layer in communication with the tracking layer, the situational awareness layer that provides output features of the various interfaces; and
   an oversight layer that combines the information from the situational awareness with the function agents to determine if processes are being performed correctly, wherein the interface shell, the one or more system agents, the one or more function agents, the dynamic documentation system, and the layering architecture that process an integrated collection of facts and relationships and to recognize deviation from or compliance with a predetermined process; and
   communicating deviation from or compliance with a predetermined process to a user.

4. An intelligent human-machine interface for an operating room, comprising:
   an interface shell;
   one or more system agents including one or more dynamic, knowledge-based software object sub-agents that model and track the state of the operating room;
   one or more function agents that model, track and facilitate operating room functions, the interface shell that provides a hardware and software interface between the system agent and the function agent;

a dynamic documentation system in communication with the one or more function agents and the one or more system agents;

a system hierarchy model of the structural elements of the operating room and a functional model;

a set of sensor, actuator, and communication systems necessary to implement functionality;

component and interface specifications for the acquisition and integration of the physical components;

functional model software specifications; and a model-based knowledge base that constructs the hierarchy and operations, wherein the interface shell, the one or more system agents, the one or more function agents, the dynamic documentation system, and the layering architecture that process an integrated collection of facts and relationships and to recognize deviation from or compliance with a predetermined process and communicate deviation from or compliance with a predetermined process to a user.

5. An intelligent human-machine interface for an operating room, comprising:

an interface shell;

one or more system agents including one or more dynamic, knowledge-based software object sub-agents that model and track the state of the operating room;

one or more function agents that model, track, and facilitate operating room functions, the interface shell that provides a hardware and software interface between the system agent and the function agent;

a dynamic documentation system in communication with the one or more function agents and the one or more system agents;

comprising a layering architecture, comprising:

a tracking layer;

an equipment and supply management layer that takes the information from the tracking layer and processes the information in regards to records, inventory and maintenance systems;

a coordination layer that takes information from the tracking layer and the equipment and supply management layer to develop an image of what is occurring in comparison to what an overall plan is based;

a situational awareness layer in communication with the tracking layer, the situational awareness layer that provides output features of the various interfaces; and an oversight layer that combines the information from the situational awareness with the function agents to determine if processes are being performed correctly, wherein the interface shell, the one or more system agents, the one or more function agents, the dynamic documentation system, and the layering architecture that process an integrated collection of facts and relationships and to recognize deviation from or compliance with a predetermined process and communicate deviation from or compliance with a predetermined process to a user.

6. An intelligent human-machine interface for an operating room, comprising:

an interface shell; one or more system agents including one or more dynamic, knowledge-based software object sub-agents that model and track the state of the operating room;

one or more function agents that model, track, and facilitate operating room functions, the interface shell that provides a hardware and software interface between the system agent and the function agent;

a dynamic documentation system in communication with the one or more function agents and the one or more system agents;

comprising a layering architecture, comprising:

a tracking layer;

an equipment and supply management layer that takes the information from the tracking layer and processes the information in regards to records, inventory and maintenance systems;

a coordination layer that takes information from the tracking layer and the equipment and supply management layer to develop an image of what is occurring in comparison to what an overall plan is based;

a situational awareness layer in communication with the tracking layer, the situational awareness layer that provides output features of the various interfaces; and an oversight layer that combines the information from the situational awareness layer with the one or more function agents to determine if processes are being performed correctly, wherein the agent and object based software architecture provides easy adaptability and expandability for the fast and efficient transmission of information between agents in the form of software robots, wherein the interface shell, the one or more system agents, the one or more function agents, the dynamic documentation system, and the layering architecture that process an integrated collection of facts and relationships and to recognize deviation from or compliance with a predetermined process and communicate deviation from or compliance with a predetermined process to a user.

* * * * *